United States Patent
Pratt et al.

(10) Patent No.: US 7,198,651 B2
(45) Date of Patent: Apr. 3, 2007

(54) METHOD OF EFFECTING A REVERSIBLE COLOR CHANGE OF DYED HAIR

(75) Inventors: Dominic Pratt, Darmstadt (DE); Masayoshi Nojiri, Tokyo (JP); Toshio Kawagishi, Minamiashigara (JP)

(73) Assignees: Kao Corporation, Tokyo (JP); Fuji Photo Film Co., Ltd., Minamiashigara (JP)

( * ) Notice: Subject to any disclaimer, the term of this patent is extended or adjusted under 35 U.S.C. 154(b) by 321 days.

(21) Appl. No.: 10/996,376

(22) Filed: Nov. 26, 2004

(65) Prior Publication Data

US 2005/0210605 A1    Sep. 29, 2005

(30) Foreign Application Priority Data

Nov. 28, 2003  (EP) .................................. 03027429

(51) Int. Cl.
*A61K 7/13*    (2006.01)

(52) U.S. Cl. ...................... 8/405; 8/407; 8/437; 8/451; 8/466; 8/570; 8/573; 8/575; 548/123; 132/202; 132/208; 534/774

(58) Field of Classification Search ................... 8/405, 8/407, 437, 451, 466, 570, 573, 575; 548/123; 132/202, 208; 534/774
See application file for complete search history.

(56) References Cited

U.S. PATENT DOCUMENTS 5,691,458 A * 11/1997 Arnost et al. ............... 534/774

OTHER PUBLICATIONS

STIC Search Report dated Oct. 2, 2006.*

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The present invention relates to a method to achieve a reversible change of the colour of hair dyed with an azo dye wherein the change of the colour can be effected by, for example, the salonist or the consumer in a simple manner.

The colour of the hair thus dyed may be changed simply by treating the dyed hair with an acid treatment composition at any time after the first dyeing treatment. If desired by the consumer, the colour may be returned to substantially the original post dye colour by treating the hair further with an alkaline treatment composition.

15 Claims, No Drawings

METHOD OF EFFECTING A REVERSIBLE COLOR CHANGE OF DYED HAIR

FIELD OF THE INVENTION

The present invention relates to a hair dyeing method using azo dyes. Such hair dye composition provides for example high dyeing power, can strongly impart the hair with extremely vivid colour, has less colour fade over time and can deliver a wide range of colours.

BACKGROUND OF THE INVENTION

Hair dyes can be classified by the dye to be used or by whether they have any bleaching action on melanin. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and at least one direct dye such as an acid dye, a basic dye or a nitro dye.

The above-described permanent hair dye is however accompanied with the drawbacks that the colour tone imparted by an oxidation dye is not so vivid and that the colour of the hair dyed with a vivid-colour producing nitro dye ordinarily employed as a direct dye markedly fades over time and becomes dull quickly even if the colour tone immediately after dyeing is very vivid (Japanese Patent Application Laid-Open (Kokai) No. Hei 6-271435).

It is a common practice to combine direct dyes and oxidative dyes in permanent products to provide more vivid colour; however, currently available direct dyes do not usually perform satisfactorily. The number of direct dyestuff that can be used in combination with oxidative dyes is limited by the necessity that they are stable to alkaline peroxide during the dyeing process. In addition, there are limitations to the types of dyes that can be used by other factors such as the molecular size or solubility of the dyestuff.

A variety of cationic direct dyes and nitro dyes have been used in permanent hair dye products to add brilliance and vividness to shades. However, in both cases the colour fades very quickly due to the loss of the direct dye from washing and light, especially on damaged or porous hair. Hair colouring is popular and many people change their hair colour using such hair dyes as described above. Typically, when one wants to change the colour of their hair, the hair must be recoloured. Currently, there appears to be no technology known, whereby the consumer or the hairdresser can change the hair colour to suit their needs and/or desires without recolouring the hair each time using dyes.

SUMMARY OF THE INVENTION

The present invention relates to a method of effecting a change of colour of hair, having the following steps: (a) dyeing the hair to a first colour with an aqueous alkaline dyeing composition having at least one azo dye of formula (I):

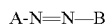
    A—N=N—B                                    (I)

wherein "A" is a monovalent group, which binds an azo group with a carbon atom, and which is free of carboxy (—CO$_2$H) groups, sulfo groups (SO$_3$H) or quaternary ammonium groups, and B is a monovalent group containing a dissociative proton and, which is free of carboxy (—CO$_2$H) or sulfo groups (—SO$_3$H) or quaternary ammonium groups, wherein the azo dye of formula (I) is capable of reversible colour change of hair in an aqueous medium;

(b) rinsing the dyed hair with water, optionally drying the hair, and (c) subsequently treating the dyed hair with an aqueous acid formulation not containing substantially any dye, wherein the colour of the hair is changed to a second colour.

In a preferred embodiment, the method further includes the step of treating the hair with an aqueous alkaline formulation not containing substantially any dye, whereby the hair colour changes to substantially the original dyed colour.

DETAILED DESCRIPTION OF THE INVENTION

The present invention relates to a method to achieve a reversible change of the colour of hair dyed wherein the change of the colour can be effected by, for example, the salonist or the consumer in a simple manner.

The colour of the hair thus dyed may be changed simply by treating the dyed hair with an acid treatment composition at any time after the first dyeing treatment. If desired by the consumer, the colour may be returned to substantially the original post dye colour by treating the hair further with an alkaline treatment composition.

In the present invention, a method of effecting a change of colour of hair includes the steps of dyeing the hair to a first colour with an aqueous alkaline dyeing composition as described in detail below, rinsing the dyed hair with water (optionally drying the hair) and subsequently treating the dyed hair with an aqueous acid formulation not containing substantially any dye, wherein the colour of the hair is changed to a second colour. Optionally, the preferred method further includes a step of treating the hair with an aqueous alkaline formulation not containing substantially any dye, whereby the hair colour changes back to substantially the first (e.g. original) colour resulting from the initial dyeing step. As a result, a method of effecting a reversible colour change of hair can be achieved.

The treatments with the acid and/or alkaline treatment compositions can be performed at any time after the initial dyeing treatment. Further, the method of effecting a reversible change of colour can be applied as often as necessary and the colour of the hair can be changed as many times as the consumer desires. If desired, the hair colour change between the first colour and the second colour continually can be repeated by further treating the hair with an aqueous acid formulation and then an aqueous alkaline formulation (both formulations not containing substantially any dye) without the use of dye containing compositions.

The present inventors have found that hair dyed with an aqueous alkaline composition containing at least one azo dye of the general structure (I) below has, for example, a vivid colour selected from a wide range of different colours without decomposition of the dye upon hair dyeing, and exhibits excellent resistance to fading from light, washing, perspiration, friction and heat. The method of effecting a change of colour of hair includes first dyeing the hair to a first colour with an aqueous alkaline dyeing composition. The hair dye composition contains at least one azo dye represented by the following formula (1):

    A—N=N—B                                   Formula (1)

where "A" represents a monovalent group, optionally substituted hetero-ring or an optionally substituted phenyl or naphthyl group, which binds an azo group with a carbon atom, and which is free of carboxy (—$CO_2H$) groups, sulfo (—$SO_3H$) groups, or quaternary ammonium groups; and "B" represents a monovalent group, optionally substituted a heterocyclic, aromatic or alkyl group, containing a dissociative proton, which is free of carboxy (—$CO_2H$), sulfo (—$SO_3H$) or quaternary ammonium groups. The azo dye is capable of reversible colour change of hair in an aqueous medium.

Formula (1) may preferably be known as a dissociative azo dye, meaning it has dissociable properties. A dye having dissociable properties means a dye having a proton capable of dissociating from the moiety "B" in formula (1) at a given pH. For example, for blue dyestuff, it is preferred that the pKa value is between about 4 and 8 to have such dissociable properties, and for yellow or red dyestuff, it is preferred that the pKa value is from about 5.3 to 8 to have such dissociable properties. As used herein, the colour "blue" refers to dyestuffs reflecting light between wavelengths of from about 500 nm to 400 nm, "red" refers to dyestuffs reflecting light between wavelengths of from about 700 nm to 600 nm and "yellow" refers to dyestuffs reflecting light between wavelengths of from about 600 nm to 550 nm.

The monovalent group represented by "A" is preferably a phenyl, naphthyl or 5-membered or 6-membered hetero-ring including at least one hetero atom selected from oxygen atom, sulfur atom or nitrogen atom within the ring. The monovalent group is preferably a substituted heterocyclic phenyl or naphthyl group. Also preferably, the monovalent phenyl, naphthyl or hetero-ring is aromatic. The monovalent group represented by "A" may be a ring condensed with another ring. Among such condensed groups, preferably, ring-condensed groups with a 5-membered or 6-membered ring are preferable. The number of carbon atoms in the heterocyclic or carbocyclic-ring (that may include substituents on the heterocyclic or carbocyclic-ring), is preferably 2 to 20, more preferably 2 to 10.

The monovalent group represented by "A" is preferably derived from a diazo component. Herein, the diazo component means a partial structure introduced by converting a heterocyclic or carbocyclic-ring compound containing an amino substituent to a diazo compound, subjecting a diazo-coupling reaction with the resulting diazo compound and a coupler, which belongs to a concept commonly used in the field of azo dyes.

In other words, the diazo component means a substituent prepared by eliminating an amino group from an amino-substituted heterocyclic or carbocyclic-ring compound possibly subjected to a diazo reaction, to render the resulting product that is a monovalent group.

The number of carbon atoms in the phenyl or naphthyl group including optional substituents is preferably from 6 to 20, more preferably from 6 to 10.

When "A" is a phenyl or naphthyl group, it preferably is derived from a diazo component as described above.

In formula (1), the monovalent group, preferably the hetero-ring, the phenyl group or the naphthyl group represented by "A" may contain one or more substituents, wherein 2 or more substituents may be the same or different groups. Examples of the substituents include for example halogen atom, alkyl group (including cycloalkyl group), alkenyl group (including cycloalkenyl group), alkynyl group, aryl group, hetero-ring group, cyano group, hydroxyl group, nitro group, alkoxyl group, aryloxy group, silyloxy group, hetero-ring oxy group, acyloxy group, carbamoyloxy group, alkoxycarbonyloxy group, aryloxycarbonyloxy, amino group (including anilino group), acylamino group, aminocarbonylamino group, alkoxycarbonylamino group, aryloxycarbonylamino group, sulfamoylamino group, alkyl-sulfonylamino group, arylsulfonylamino group, mercapto group, alkylthio group, arylthio group, hetero-ring thio group, sulfamoyl group, alkylsulfinyl group, arylsulfinyl group, alkylsulfonyl group, arylsulfonyl group, acyl group, alkoxycarbonyl group, aryloxycarbonyl group, carbamoyl group, arylazo group, hetero-ring azo group, imide group, phosphino group, phosphinyl group, phosphinyloxy group, phosphinylamino group, and silyl group. More specifically, the substituent includes for example a halogen atom (for example, chlorine atom, bromine atom, iodine atom), an alkyl group (linear or branched or cyclic alkyl group with one to 10 carbon atoms, preferably one to 6 carbon atoms, for example, methyl, ethyl, n-propyl, isopropyl, t-butyl, n-octyl, 2-chloroethyl, 2-cyanoethyl, 2-ethylhexyl, cyclopropyl, cyclopentyl), alkenyl group (linear or branched or cyclic alkenyl group with 2 to 10 carbon atoms, preferably 2 to 6 carbon atoms, for example, vinyl, allyl, prenyl, cyclopenten-1-yl), alkynyl group (alkynyl group with 2 to 10 carbon atoms, preferably 2 to 6 carbon atoms, for example, ethynyl, propargyl), aryl group (aryl group with 6 to 12 carbon atoms, preferably 6 to 8 carbon atoms, for example, phenyl, p-tolyl, naphthyl, 3-chlorophenyl, 2-aminophenyl), hetero-ring group (monovalent group with one to 12 carbon atoms, preferably 2 to 6 carbon atoms, which is recovered by eliminating one hydrogen atom from an aromatic or non-aromatic hetero-ring compound, 5-membered or 6-membered; for example, 1-pyrazolyl, 1-imidazolyl, 2-furyl, 2-thienyl, 4-pyrimidinyl, 2-benzothiazolyl), cyano group, hydroxyl group, nitro group, alkoxy group (linear or branched or cyclic alkoxy group with one to 10 carbon atoms, preferably one to 6 carbon atoms, for example, methoxy, ethoxy, isopropoxy, t-butoxy, cyclopentyloxy, 2-buten-1-yloxy, 2-methoxyethoxy), aryloxy group (aryloxy group with 6 to 12 carbon atoms, preferably 6 to 8 carbon atoms, for example, phenoxy, 2-methylphenoxy, 4-t-butylphenoxy, 3-nitrophenoxy), silyloxy group (silyloxy group with 3 to 10 carbon atoms, preferably 3 to 6 carbon atoms, for example, trimethylsilyloxy, t-butyldimethylsilyloxy), hetero-ring oxy group (hetero-ring oxy group with one to 12 carbon atoms, preferably 2 to 6 carbon atoms, for example, 1-phenyltetrazole-5-oxy, 2-tetrahydropyranyloxy), acyloxy group (acyloxy group with one to 12 carbon atoms, preferably one to 8 carbon atoms, for example, formyloxy group, acetyloxy, pivaloyloxy, benzoyloxy, p-methoxyphenylcarbonyloxy), carbamoyloxy group (carbamoyloxy group with one to 10 carbon atoms, preferably one to 6 carbon atoms, for example, N,N-dimethylcarbamoyloxy, N,N-diethylcarbamoyloxy, morpholinocarbonyloxy, N-n-octylcarbamoyloxy), alkoxycarbonyloxy group (alkoxycarbonyloxy group with 2 to 10 carbon atoms, preferably 2 to 6 carbon atoms, for example, methoxycarbonyloxy, ethoxycarbonyloxy, t-butoxycarbonyloxy, n-octyloxycarbonyloxy), aryloxycarbonyloxy group (aryloxycarbonyloxy group with 7 to 12 carbon atoms, preferably 7 to 10 carbon atoms, for example, phenoxycarbonyloxy, p-methoxyphenoxycarbonyloxy), amino group (amino group, alkylamino group with one to 10 carbon atoms, preferably one to 6 carbon atoms, anilino group with 6 to 12 carbon atoms, preferably 6 to 8 carbon atoms, or hetero-ring amino group with one to 12 carbon atoms, preferably 2 to 6 carbon atoms, including for example amino, methylamino, dimethylamino, anilino, N-methyl-anilino, diphenylamino, imidazol-2-ylamino, pyrazol-3-ylamino), acylamino group (alkylcarbonylamino group with one to 10 carbon atoms, preferably one to 6 carbon atoms, arylcarbonylamino group with 6 to 12 carbon atoms, preferably 6 to 8 carbon atoms, or hetero-ring carbonylamino group with 2 to 12 carbon atoms, preferably 2 to 6 carbon atoms, including for example formylamino, acetylamino, pivaloylamino, benzoylamino, pyridine-4-carbonylamino, thiophene-2-carbonylamino), aminocarbonylamino group (aminocarbonylamino with one to 12 carbon atoms, preferably one to 6 carbon atoms, for example, carbamoylamino, N,N-dimethylaminocarbonylamino, N,N-diethylaminocarbonylamino, morpholin-4-ylcarbonylamino), alkoxycarbonylamino group (alkoxycarbonylamino group with 2 to 10 carbon atoms, preferably 2 to 6 carbon atoms, for example, methoxycarbonylamino, ethoxycarbonylamino, t-butoxycarbonylamino), aryloxycarbonylamino group (aryloxycarbonylamino group with 7 to 12 carbon atoms, preferably 7 to 9 carbon atoms, for example, phenoxycarbonylamino, p-chlorophenoxycarbonylamino, 4-methoxyphenoxycarbonylamino), sulfamoylamino group (sulfamoylamino group with zero to 10 carbon atoms, preferably zero to 6 carbon atoms, for example sulfamoylamino, N,N-dimethylaminosulfonylamino, N-(2-hydroxyethyl)sulfamoylamino), alkylsulfonylamino group (alkylsulfonylamino group with one to 10 carbon atoms, preferably one to 6 carbon atoms, for example, methylsulfonylamino, butylsulfonylamino), arylsulfonylamino group (arylsulfonylamino group with 6 to 12 carbon atoms, preferably 6 to 8 carbon atoms, for example, phenylsulfonylamino, 2,3,5-trichlorophenylsulfonylamino group, p-methylphenylsulfonylamino), mercapto group, alkylthio group (alkylthio group with one to 10 carbon atoms, preferably one to 6 carbon atoms, for example methylthio, ethylethio, butylthio), arylthio group (arylthio with 6 to 12 carbon atoms, preferably 6 to 8 carbon atoms, for example, phenylthio, p-chlorophenylthio, m-methoxyphenylthio), hetero-ring thio group (hetero-ring thio group with 2 to 10 carbon atoms, preferably one to 6 carbon atoms, for example 2-benzothiazolylthio, 1-phenyltetrazol-5-ylthio), sulfamoyl group (sulfamoyl group with zero to 10 carbon atoms, preferably zero to 6 carbon atoms, for example, sulfamoyl, N-ethylsulfamoyl, N,N-dimethylsulfamoyl, N-acetylsulfamoyl, N-benzoylsulfamoyl), alkylsulfinyl group (alkylsulfinyl group with one to 10 carbon atoms, preferably one to 6 carbon atoms, for example, methylsulfinyl, ethylsulfinyl), arylsulfinyl group (arylsulfinyl group with 6 to 12 carbon atoms, preferably 6 to 8 carbon atoms, for example, phenylsulfinyl, p-methylphenylsulfinyl), alkylsulfonyl group (alkylsulfonyl group with one to 10 carbon atoms, preferably one to 6 carbon atoms, for example, methylsulfonyl, ethylsulfonyl), arylsulfonyl group (arylsulfonyl group with 6 to 12 carbon atoms, preferably 6 to 8 carbon atoms, for example, phenylsulfonyl, p-chlorophenylsulfonyl), acyl group (formyl group, alkylcarbonyl group with 2 to 10 carbon atoms, preferably 2 to 6 carbon atoms, or arylcarbonyl group with 7 to 12 carbon atoms, preferably 7 to 9 carbon atoms, including for example acetyl, pivaloyl, 2-chloroacetyl, benzoyl, 2,4-dichlorobenzoyl), alkoxycarbonyl group (alkoxycarbonyl group with 2 to 10 carbon atoms, preferably 2 to 6 carbon atoms, for example, methoxycarbonyl, ethoxycarbonyl, t-butoxycarbonyl, isobutyloxycarbonyl), aryloxycarbonyl group (aryloxycarbonyl group with 7 to 12 carbon atoms, preferably 7 to 9 carbon atoms, for example, phenoxycarbonyl, 2-chlorophenoxycarbonyl, 3-nitrophenoxycarbonyl, 4-t-butylphenoxycarbonyl), carbamoyl group (carbamoyl group with one to 10 carbon atoms, preferably one to 6 carbon atoms, for example, carbamoyl, N-methylcarbamoyl, N,N-dimethylcarbamoyl, N-(2-hydroxyethyl)carbamoyl, N-(methylsulfonyl)carbamoyl), arylazo group (arylazo group with 6 to 12 carbon atoms, preferably 6 to 8 carbon atoms, for example phenylazo, p-chlorophenylazo), hetero-ring azo group (hetero-ring azo group with one to 10 carbon atoms, preferably one to 6 carbon atoms, for example, pyrazol-3-ylazo, thiazol-2-ylazo, 5-ethylthio-1,3,4-thiadiazol-2-ylazo), imide group (imide group with 2 to 10 carbon atoms, preferably 4 to 8 carbon atoms, for example, N-succinimide, N-phthalimide), phosphino group (phosphino group with 2 to 12 carbon atoms, preferably 2 to 6 carbon atoms, for example, dimethylphosphino, diphenylphosphino, methylphenoxyphosphino), phophinyl group (phosphinyl group with 2 to 12 carbon atoms, preferably 2 to 6 carbon atoms, for example phosphinyl, diethoxyphosphinyl), phosphinyloxy group (phosphinyloxy group with 2 to 12 carbon atoms, preferably 2 to 6 carbon atoms, for example, diphenoxyphosphinyloxy, dibutoxyphosphinyloxy), phosphinylamino group (phosphinylamino group with 2 to 12 carbon atoms, preferably 2 to 6 carbon atoms, for example, dimethoxyphosphinylamino, dimethylaminophosphinylamino), and silyl group (silyl group with 3 to 12 carbon atoms, preferably 3 to 8 carbon atoms, for example, trimethylsilyl, t-butyldimethylsilyl, phenyldimethylsilyl). In case that these groups are groups with a possibility of additional substitution, these groups may further contain substituents, and preferably, such substituents then include the groups with the same meaning as described as the preferable substituent for the hetero-ring group, the phenyl group or the naphthyl group represented by "A". In case that these groups are substituted with 2 or more substituents, the substituents may be the same or different.

Particularly preferably, the substituent for the hetero-ring group, the phenyl group or the naphthyl group represented by "A" is a halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably, the substituent is a halogen atom, alkyl group, cyano group, hydroxyl group, nitro group, alkoxy group, amino group (including anilino group), acylamino group, alkylsulfonylamino group and carbamoyl group.

When the monovalent group "A" is a heterocyclic group, specific examples of suitable monovalent hetero-ring group binding via the carbon atom to the azo group are described below (A-1 to A-25), but the invention is not at all limited there to.

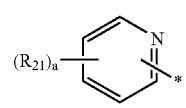

(A-1)

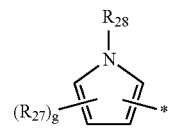

(A-7)

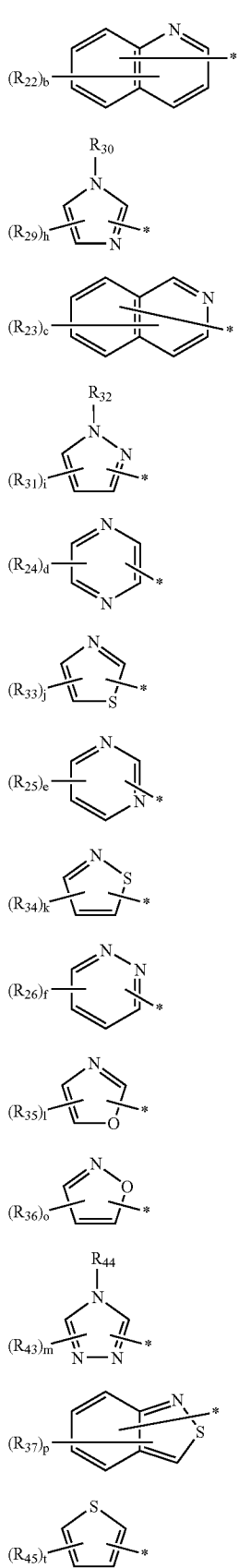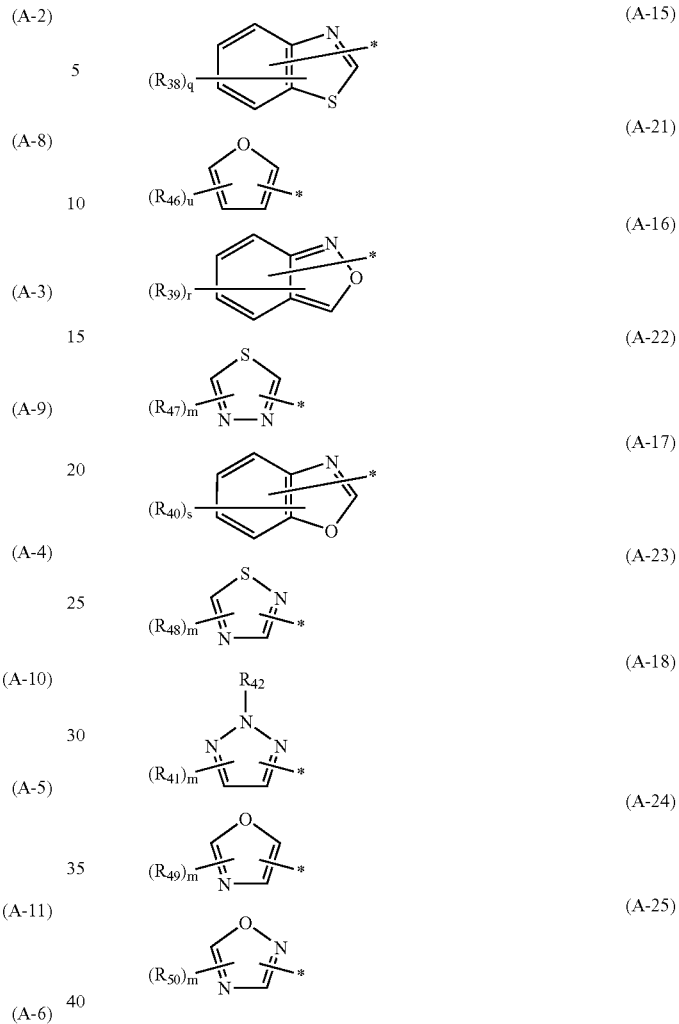

In the specific examples (A-1) to (A-25), the symbol "*" expresses the position in formula (1), at which the hetero-ring group binds to the azo group; $R_{21}$ to $R_{50}$ independently represent a hydrogen atom or a substituent. The substituent represents a group with the same meaning, as listed as the substituent for the monovalent group represented by "A", and the substituent preferably includes a halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably, the substituent is a halogen atom, alkyl group, cyano group, hydroxyl group, nitro group, alkoxy group, amino group (including anilino group), acylamino group, alkylsulfonylamino group, and carbamoyl group. "a, p, q, r, s" represent an integer of 0 to 4. "b, c" represent an integer of 0 to 6. "d, e, f, g, t, u" represent an integer of 0 to 3. "h, i, j, k, l, o" represent an integer of 0 to 2. "m" represents an integer of 0 to 1. When "a" through "u" represent an integer of 2 or more, groups represented by $R_{21}$ to $R_{50}$, which exist in a number of 2 or more, may be the same or different to each other.

Further, groups adjacent to each other as represented by $R_{21}$ to $R_{50}$ may combine together to form a ring structure. The resulting ring structure formed may be a hetero-ring or a carbon ring, and it may be a saturated ring or an unsaturated ring. The total number of the carbon atoms and the hetero atoms is 3 to 6, preferably 5 or 6.

In case that $R_{21}$ to $R_{50}$ in the formulas (A-1) to (A-25) are groups with a possibility of additional substitutions, $R_{21}$ to $R_{50}$ may further contain a substituent and the substituent in that case is the same as listed as the substituent for the monovalent group represented by "A".

In the compound represented by formula (1) in accordance with the invention, the monovalent group represented by "A" is preferably (A-1), (A-5), (A-8), (A-9), (A-10), (A-11), (A-12), (A-13), (A-14), (A-15), (A-17), (A-19), (A-22), (A-23), (A-24), and (A-25), more preferably (A-10), (A-11), (A-12), (A-14), (A-22), (A-23), and (A-25).

"B" in the azo dye represented by formula (1) represents a monovalent group for the formation of a dissociative azo dye from the compound represented by formula (1) and is preferably derived from a coupler component. Herein, the coupler component means a partial structure derived from a coupler compound capable of reacting with a diazonium salt to give an azo dye. The concept is commonly used in the field of azo dyes. "B" in the azo dye represented by formula (1) has preferably 3 to 30 carbon atoms, more preferably 3 to 20 carbon atoms, most preferably 3 to 12 carbon atoms, inclusive of the substituents therein.

Preferably "B" is a heterocyclic, aromatic or alkyl group containing a dissociate proton and is free of carboxy group, sulfo groups or quaternary ammonium groups.

The coupler component is preferably a coupler component known in the field of silver halide colour photographic materials, and as such, use can be made of the backbone moiety of a coupler for silver halide colour photographic materials (the moiety serving as a dye chromophore via coupling with an oxidized aromatic amine-based developer as a principal developing agent, such as p-phenylenediamine), which is described in detail in Research Disclosure 37038 (February 1995), page 80–85, and 87–89.

The coupler known as a coupler forming a yellow-coloured image in the field of silver halide colour photographic materials includes for example couplers of the pivaloylacetamide type, benzoylacetamide type, malondiester type, malondiamide type, dibenzoylmethane type, benzothiazolylacetamide type, malonestermonoamide type, benzoxazolylacetamide type, benzimidazolylacetamide type, cyanoacetamide type, cycloalkylcarbonylacetamide type, indolin-2-ylacetamide type, quinazolin-4-on-2-ylacetamide type described in U.S. Pat. No. 5,021,332, and the benzo-1,2,4-thiadiazine-1,1,-dioxid-3-ylacetamide type described in U.S. Pat. No. 5,021,330, the coupler described in EP 421221, the coupler described in U.S. Pat. No. 5,455,149, the coupler described in EP 0622673, the couplers of 3-indoloylacetamide type described in EP 0953871, 0953872 and 0953873, are preferred coupler backbones.

The coupler known as a coupler forming magenta-coloured image in the field of silver halide colour photographic materials includes for example couplers of the 5-pyrazolone type, 1H-pyrazolo[1,5-a]benzimidazole type, 1H-pyrazolo[5,1-c][1,2,4]triazole type, 1H-pyrazolo[1,5-b][1,2,4]triazole type, 1H-imidazo[1,2-b]pyrazole type, cyanoacetophenone type, the active propene type described in WO 93/01523, and the enamine type described in WO 93/07534, the 1H-imidazo[1,2-b][1,2,4]triazole type coupler and the coupler described in U.S. Pat. No. 4,871,652, are preferred coupler backbones.

The coupler known as a coupler forming a cyan-coloured image in the field of silver halide colour photographic materials includes for example couplers of the phenol type, naphthol type, the 2,5-diphenylimidazole type described in EP 0249453, 1H-pyrrolo[1,2-b][1,2,4]triazole type, 1H-pyrrolo[2,1-c][1,2,4]triazole type, the pyrrole type described in Japanese Patent Laid-open Nos. 188137/1992 and 190347/1992, 3-hydroxypyridine type described in Japanese Patent Laid-open No. 315736/1989, pyrrolopyrazole type described in U.S. Pat. No. 5,164,289, the pyrroloimidazole type described in Japanese Patent Laid-open No. 174429/1992, and the pyrazolopyrimidine type described in U.S. Pat. No. 4,950,585, and the pyrrolotriazine type coupler described in Japanese Patent Laid-open No. 204730/1992, the coupler described in U.S. Pat. No. 4,746,602, the coupler described in U.S. Pat. No. 5,104,783, the coupler described in U.S. Pat. No. 5,162,196, and the coupler described in EP 0556700, are preferred coupler backbones.

The group represented by "B" in the azo dye represented by formula (1) preferably includes groups represented by the following structures (B-1) to (B-12).

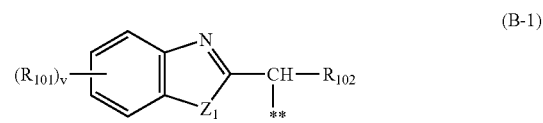

(B-1)

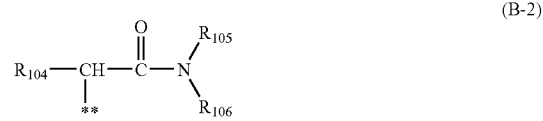

(B-2)

(B-3)

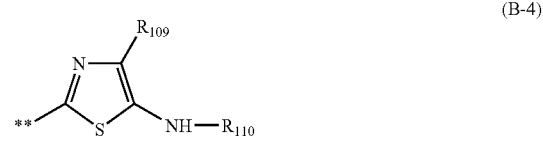

(B-4)

(B-5)

(B-6)

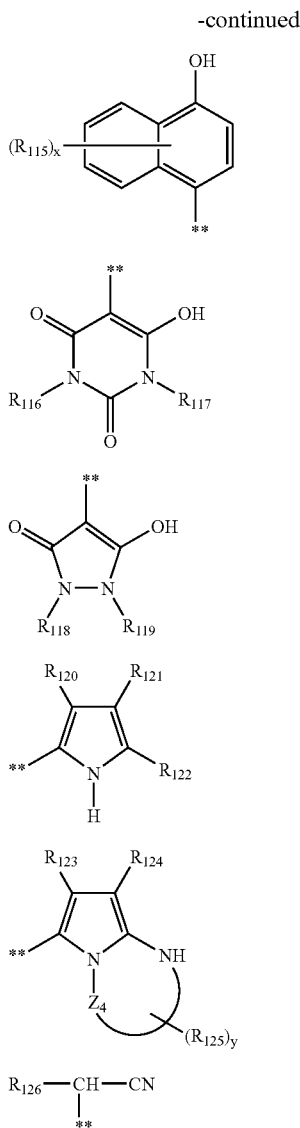

In the formulas, the symbol "**" expresses the position where the groups bind to the azo group in formula (1).

In formula (B-1), $R_{101}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group. $R_{102}$ represents cyano group, alkylsulfonyl group, arylsulfonyl group, acyl group, alkoxycarbonyl group, aryloxycarbonyl group, or carbamoyl group. $Z_1$ represents an oxygen atom, sulfur atom, or —N($R_{103}$)—. $R_{103}$ represents a hydrogen atom, alkyl group, aryl group or hetero-ring group. "v" represents an integer of 0 to 4. Provided that v is more than 1, the $R_{101}$ groups in the number "v" may be the same or different. $R_{101}$ is preferably a halogen atom, acylamino group, alkylsulfonylamino group, sulfamoyl group, and carbamoyl group. $R_{102}$ is preferably a cyano group, and a carbamoyl group. $Z_1$ is preferably an oxygen atom, sulfur atom, or —N($R_{103}$)— where $R_{103}$ is an alkyl group.

In formula (B-2), $R_{104}$ represents a cyano group, alkylsulfonyl group, arylsulfonyl group, acyl group, alkoxycarbonyl group, aryloxycarbonyl group, or carbamoyl group; $R_{105}$ and $R_{106}$ independently represent a hydrogen atom, alkyl group, aryl group, or hetero-ring group. Preferably, $R_{104}$ is a cyano group, acyl group, and carbamoyl group, while one of $R_{105}$ and $R_{106}$ is preferably a hydrogen atom.

In formula (B-3), $R_{107}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)=, or —N=; $R_{108}$ represents an alkyl group, aryl group, hetero-ring group, alkylthio group, arylthio group, alkoxycarbonyl group, or carbamoyl group. Provided that $Z_2$ and $Z_3$ both represent —C($R_{108}$)=, two $R_{108}$ groups may be the same or different or may bind together to form a carbon ring or a hetero-ring. $R_{107}$ is preferably a hydrogen atom, alkyl group and aryl group, more preferably a hydrogen atom and alkyl group, and $R_{108}$ is preferably an alkyl group, aryl group, and hetero-ring group, more preferably an alkyl group.

In formula (B-4), $R_{109}$ represents an alkyl group, aryl group or hetero-ring group, and $R_{110}$ represents a hydrogen atom, alkyl group, aryl group, hetero-ring group, acyl group, alkylsulfonyl group or arylsulfonyl group. $R_{109}$ is preferably an alkyl group and aryl group, and $R_{110}$ is preferably a hydrogen atom and alkyl group.

In formula (B-5), $R_{111}$ represents an alkyl group, aryl group, alkoxy group, amino group (including anilino group), alkoxycarbonyl group, cyano group, acylamino group, or carbamoyl group; $R_{112}$ represents a hydrogen atom, alkyl group, aryl group, or hetero-ring group; $R_{113}$ represents a hydroxyl group or amino group. $R_{111}$ is preferably an alkoxycarbonyl group, cyano group, and carbamoyl group; $R_{112}$ is preferably an alkyl group and aryl group.

In formula (B-6), $R_{114}$ represents a halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, heteroring thio group, alkoxycarbonyl group, or carbamoyl group; "w" represents an integer of 0 to 4. Provided that "w" is 2 to 4, the $R_{114}$ groups may be the same or different. $R_{114}$ is preferably a halogen atom, alkyl group, acylamino group, alkoxycarbonylamino group, aminocarbonylamino group, alkylsulfonylamino group, arylsulfonylamino group, and carbamoyl group, more preferably halogen atom, alkyl group, acylamino group, and alkylsulfonylamino group.

In formula (B-7), $R_{115}$ represents a halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, heteroring thio group, alkoxycarbonyl group, carbamoyl group, or "x" represents an integer of 0 to 6. Provided that "x" is 2 to 6, the $R_{115}$ groups may be the same or different. $R_{115}$ is preferably a halogen atom, acylamino group, alkoxycarbonylamino group, aminocarbonylamino group, alkylsulfonylamino group, arylsulfonylamino group, and carbamoyl group, more preferably an acylamino group, alkylsulfonylamino group, and carbamoyl group.

In formula (B-8), $R_{116}$ and $R_{117}$ independently represent alkyl group or aryl group, and these groups are preferably the same to each other.

In formula (B-9), $R_{118}$ and $R_{119}$ independently represent alkyl group or aryl group, and these groups are preferably the same to each other.

In formula (B-10), $R_{120}$ and $R_{121}$ independently represents an alkyl group, aryl group, hetero-ring group, cyano group, alkylsulfonyl group, arylsulfonyl group, alkoxycarbonyl group, or carbamoyl group; $R_{122}$ represents a hydrogen atom, alkyl group, aryl group, hetero-ring group, acylamino group, alkylsulfonylamino group, or arylsulfonylamino group. Preferably, $R_{120}$ and $R_{121}$ are an alkyl group, aryl group, hetero-ring group, and cyano group. Preferably, $R_{122}$ is a hydrogen atom, alkyl group, aryl group, acylamino group, and alkylsulfonylamino group.

In formula (B-11), $R_{123}$ and $R_{124}$ independently represents an alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and one carbon atom. $R_{125}$ represents an alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of 0 to 2, provided that $Z_4$ forms a 5-membered ring; and "y" represents an integer of 0 to 3, provided that $Z_4$ forms a 6-membered ring. Preferably, $R_{123}$ is an alkyl group, aryl group, hetero-ring group, and cyano group. Preferably, $R_{124}$ is an alkylsulfonyl group, arylsulfonyl group, alkoxycarbonyl group, and carbamoyl group. $R_{125}$ is preferably an alkyl group, aryl group, alkylthio group, amino group, and acylamino group. In formula (B-12), $R_{126}$ represents an alkyl group, acyl group, aroyl group or aryl group.

In formulas (B-1) to (B-12), preferable carbon numbers and specific examples of the individual groups listed in the descriptions of the groups represented by $R_{101}$ to $R_{126}$ are the same as those listed in the description of the substituent for the hetero-ring group, the phenyl group or the naphthyl group represented by "A".

In case that $R_{101}$ to $R_{126}$ in formulas (B-1) to (B-12) are groups with a possibility of additional substitution, $R_{101}$ to $R_{126}$ may further have a substituent, and the substituent in that case is the same as the substituent listed for the hetero-ring group, the phenyl group or the naphthyl group represented by "A".

Dyes represented by the following formulas DS-1 to DS-6 among compounds represented by formula (1) are particularly preferable. "A" in formulas DS-1 to DS-6 represents a group with the same meaning as that of "A" in formula (1).

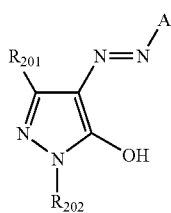

DS-1

-continued

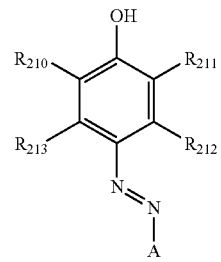

DS-2

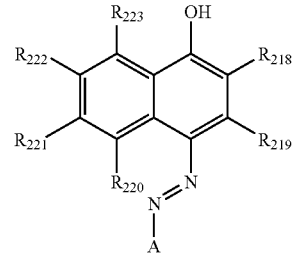

DS-3

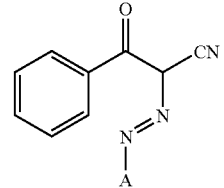

DS-4

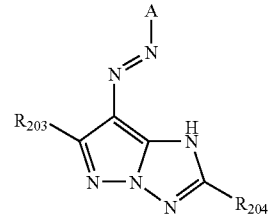

DS-5

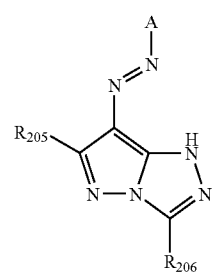

DS-6

In formula DS-1, $R_{201}$ represents an alkyl group, aryl group, alkoxy group, amino group (including anilino group), alkoxycarbonyl group, cyano group, acylamino group, or carbamoyl group; $R_{202}$ represents a hydrogen atom, alkyl group, aryl group, or hetero-ring group. Preferably, $R_{201}$ is an alkoxycarbonyl group, cyano group, and carbamoyl group and $R_{202}$ is an alkyl group and aryl group.

In formula DS-2, $R_{210}$ and $R_{211}$ represent a hydrogen atom, halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; $R_{212}$ and $R_{213}$ represent a hydrogen atom, halogen atom, alkyl group, alkoxy group, or acylamino group. $R_{210}$ and $R_{211}$ preferably represent a hydrogen atom, chlorine atom, bromine atom, alkyl group, and acylamino group, and more preferably at least one of $R_{210}$ and $R_{211}$ is a hydrogen atom.

In formula DS-3, $R_{218}$ represents a hydrogen atom, halogen atom, alkyl group, aryl group, acylamino group, alkylsulfonylamino group, arylsulfonylamino group, alkoxycarbonyl group, aminocarbonylamino group, carbamoyl group, or sulfamoyl group; $R_{220}$ and $R_{223}$ represents a hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ represents a hydrogen atom, chlorine atom, bromine atom, alkyl group, and acylamino group. $R_{218}$ is preferably a hydrogen atom, acylamino group, alkylsulfonylamino group, arylsulfonylamino group, alkoxycarbonyl group, aminocarbonylamino group, carbamoyl group, and sulfamoyl group. $R_{220}$ and $R_{223}$ are preferably a hydrogen atom, acylamino group, alkoxycarbonylamino group, and alkylsulfonylamino group. $R_{219}$, $R_{221}$, and $R_{222}$ are preferably a hydrogen atom.

In the formula DS-5, $R_{203}$ represents hydrogen atom, alkyl group, aryl group, hetero-ring group, alkoxyl group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{204}$ represents alkyl group, aryl group, or hetero-ring group. $R_{203}$ is preferably hydrogen atom and alkyl group, and the alkyl group particularly preferably includes methyl group, ethyl group, isopropyl group, and t-butyl group. $R_{204}$ is most preferably alkyl group.

In the formula DS-6, $R_{205}$ represents hydrogen atom, alkyl group, aryl group, hetero-ring group, alkoxyl group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{206}$ represents alkyl group, aryl group, hetero-ring group, alkylthio group, arylthio group, alkoxycarbonyl group, or carbamoyl group. $R_{205}$ is preferably hydrogen atom and alkyl group, and the alkyl group particularly preferably includes methyl group, ethyl group, isopropyl group, and t-butyl group. $R_{206}$ is preferably alkyl group, aryl group, or alkylthio group, most preferably alkyl group.

In formulas DS-1 to DS-6, preferable carbon numbers and specific examples of the individual groups listed in the descriptions of the groups represented by $R_{201}$ to $R_{206}$, $R_{210}$ to $R_{213}$ and $R_{218}$ to $R_{223}$ are the same as those listed in the description of the substituent for the monovalent group represented by "A".

Provided that $R_{201}$ to $R_{206}$, $R_{210}$ to $R_{213}$ and $R_{218}$ to $R_{223}$ in formulas DS-1 to DS-6 are groups with a possibility of additional substitution, these radicals may have additional substituents. The substituents then are the same as those listed in the description of the substituent for the hetero-ring group, the phenyl group and the naphthyl group represented by "A".

Specific compound examples of the azo dye represented by formula (1) that are preferably suitable for imparting a new colour to the hair and also capable of reversible colour change of hair in an aqueous medium in accordance with the method of the invention are described below, but the invention is not limited to these examples.

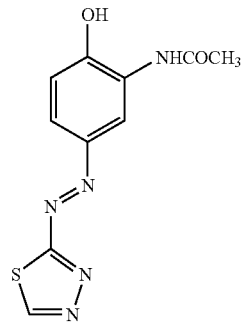

Dye 1

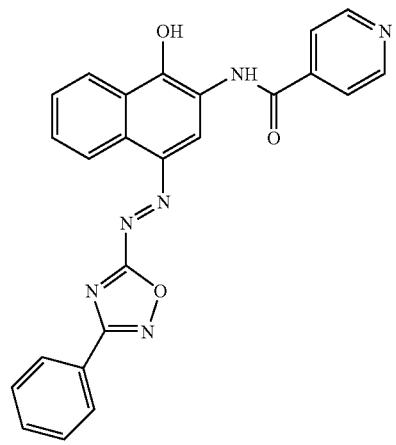

Dye 2

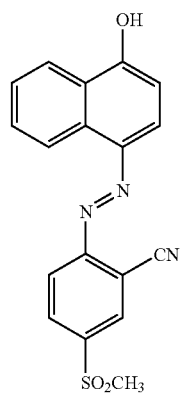

Dye 3

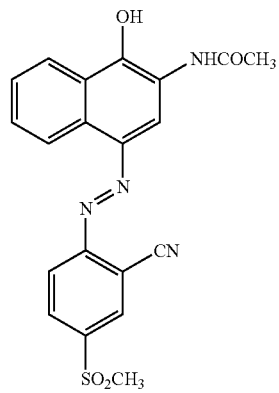

Dye 4

-continued
Dye 5
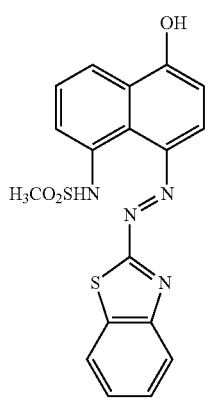
Dye 6
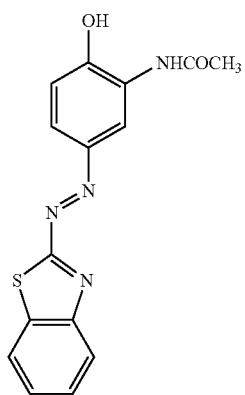
Dye 7
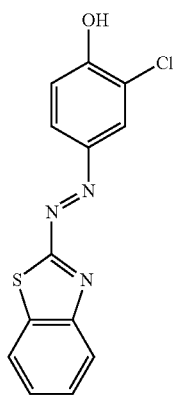
Dye 8
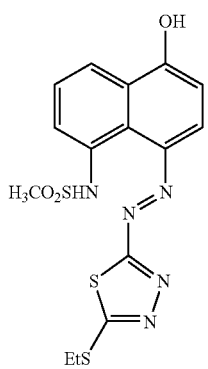
Dye 9
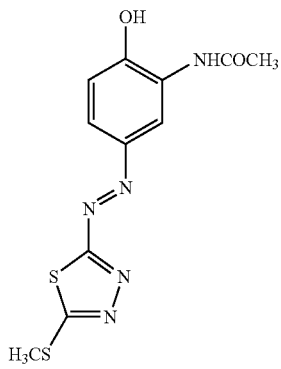
Dye 10
Dye 11
Dye 12

Dye 13
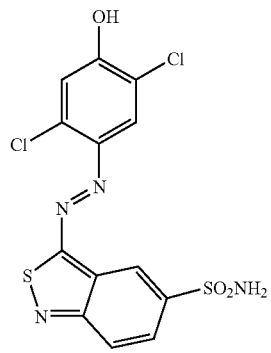
Dye 17
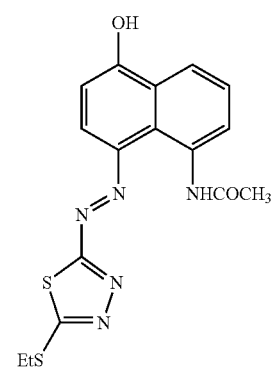
Dye 14
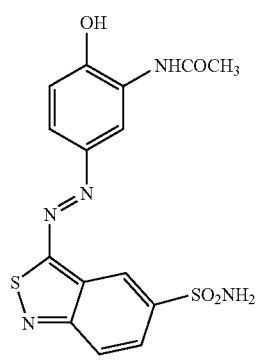
Dye 18
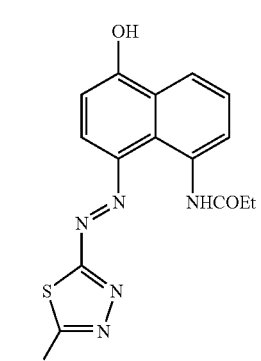
Dye 15
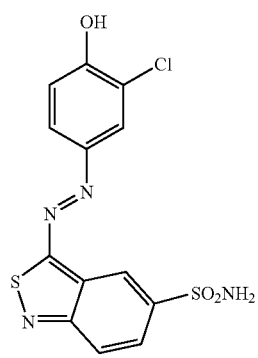
Dye 19
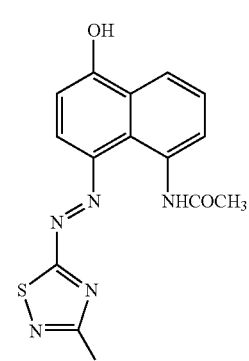
Dye 16
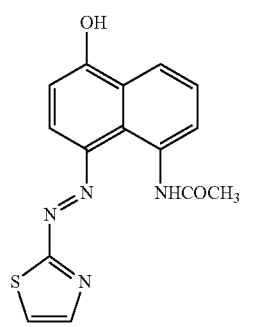
Dye 20
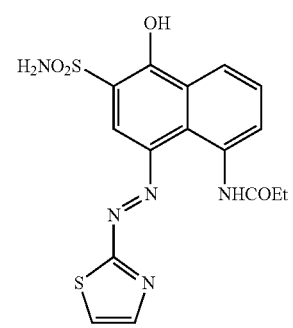

-continued

Dye 21
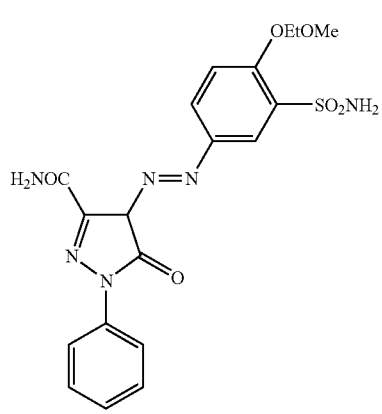

Dye 22
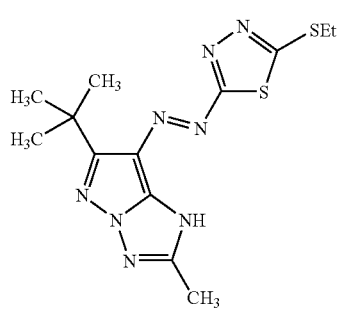

Dye 23
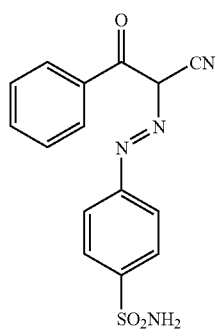

Dye 24
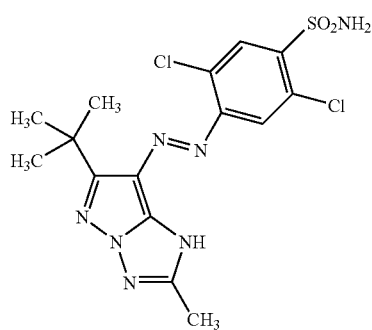

It is particularly preferred for performing the reversible change of the colour to effect the basic dyeing of the hair by using a dye where the "A" group in formula (I) contains a proton with a pKa value between 4 and 8, more preferably between 4.2 and 7.5 and most preferably between 4.4 and 7.5 for blue dyes or a pKa value between 5.3 and 8, more preferably 5.4 and 7.5 and most preferably between 5.5 and 7.0 for yellow or red dyes.

Preferably, the colour change that may be measured by the value of delta E (see the description of the examples) after the acid treatment is greater than 10 in order to see the change of the colour. Delta E is measured as follows: an aqueous alkaline dyeing composition containing a dye having a concentration of 0.1% or 0.2% is used to dye undamaged white goat hair (L=84, a=0 and b=12) by applying for 30 minutes at 30 Celsius. Subsequently, the hair is treated with an acidic composition (pH 2.5) for one minute. As mentioned above, the hair colour undergoes a delta E colour change after the acid treatment of preferably greater than 10, more preferably greater than 12. Furthermore, when subsequently treated with an alkaline composition (such as for example, pH 10), the delta E colour change versus the original dyed colour is preferably less than 4, more preferably less than 3. One or more of the above mentioned, particularly preferred azo direct dyes can be used. The dyeing composition may contain any other known dye(s) such as other direct dyes or oxidative dyes.

Examples of additional dyes that may be used in combination with the direct dyes of the invention include, dyes of formula I not capable of reversible color change of hair in an aqueous medium, such as:

Dye 25
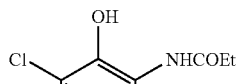
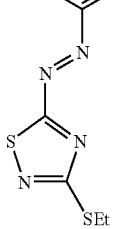

Dye 26
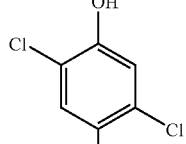
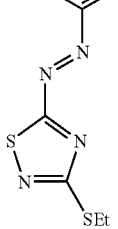

Dye 27
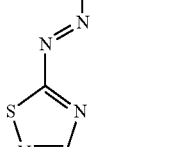
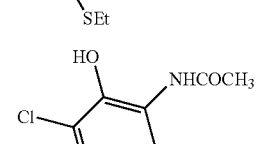
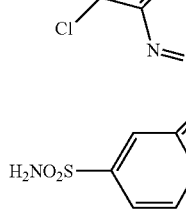

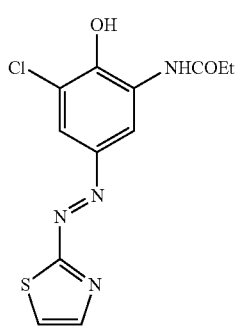
Dye 28
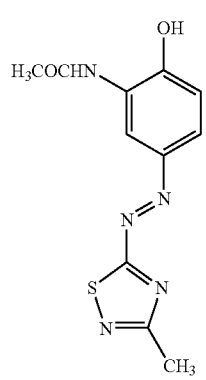
Dye 32
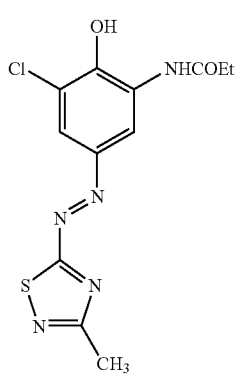
Dye 29
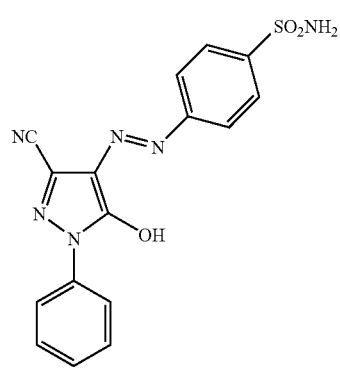
Dye 33
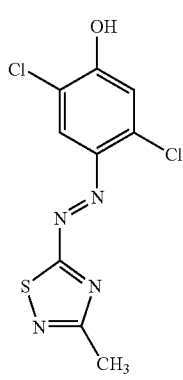
Dye 30
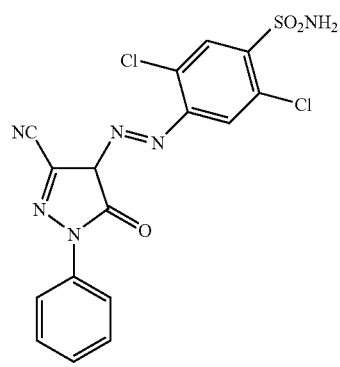
Dye 34
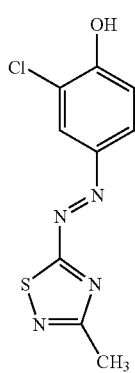
Dye 31
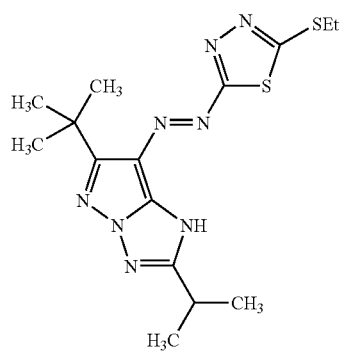
Dye 35

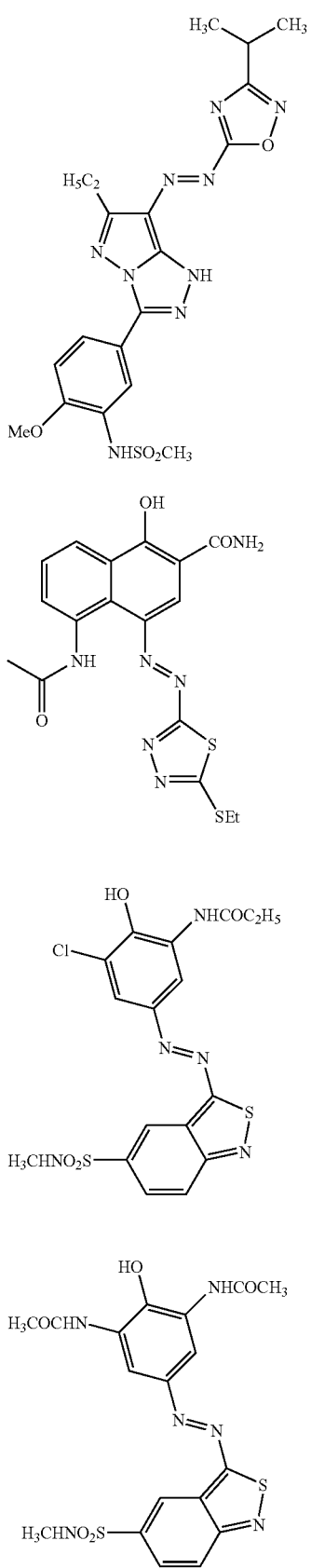
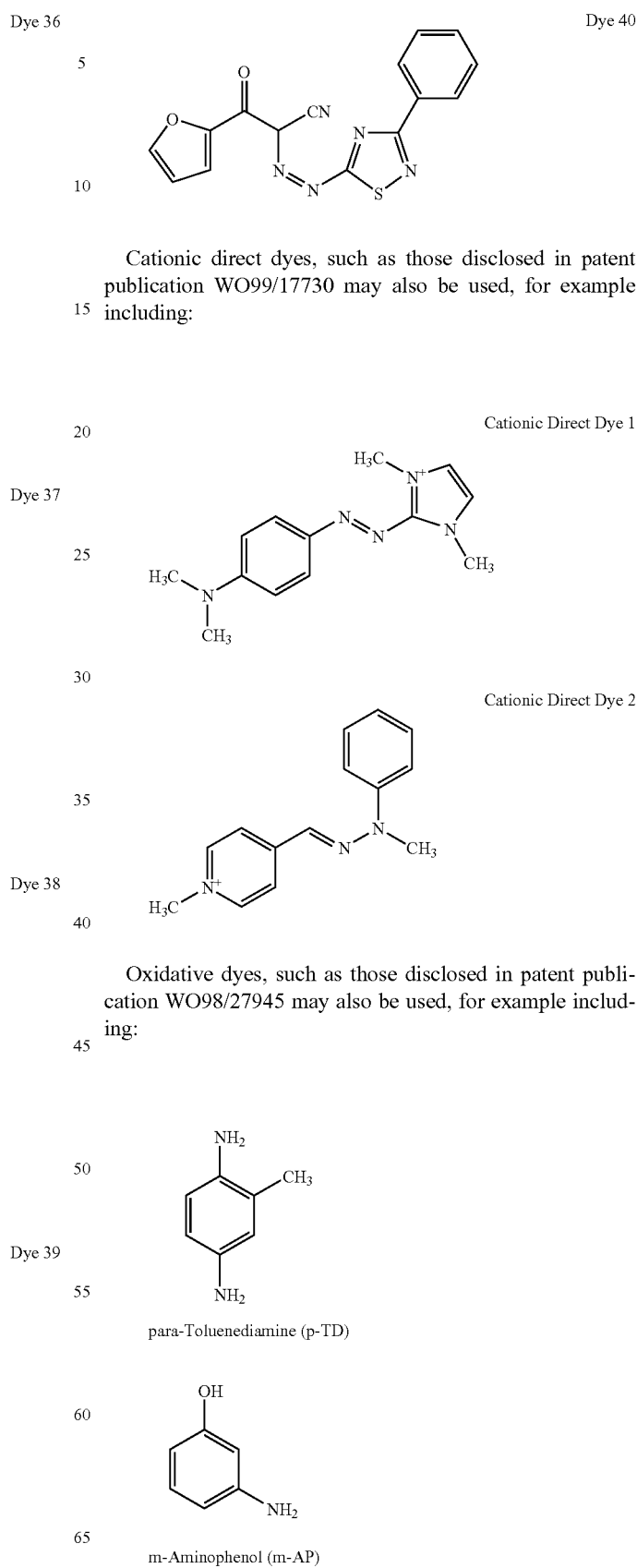
Cationic direct dyes, such as those disclosed in patent publication WO99/17730 may also be used, for example including:
Oxidative dyes, such as those disclosed in patent publication WO98/27945 may also be used, for example including:

-continued

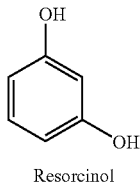
Resorcinol and other common direct dyes used for hair coloring. For example, non-oxidative dyes as disclosed in patent publication WO01/28508.

The azo dyes represented by the formula (I) capable of reversible color change of hair in an aqueous medium as defined in the examples are preferably added in an amount of from 0.01 to 20 wt. %, more preferably from 0.05 to 10 wt. %, even more preferably from 0.1 to 5 wt. % based on the whole composition (e.g. when applicable, after mixing of all the component parts when the composition is a two part or three part composition; this definition will be applied equally hereinafter). When another direct dye is used in combination, the total amount of this dye together with the direct dye of formula (I) capable of a reversible color change of hair in an aqueous medium as defined in the examples is preferably from 0.01 to 20 wt. %, more preferably from 0.05 to 10 wt. %, even more preferably from 0.1 to 5 wt. %, based on the whole composition. When such combination is used, the amount of the other direct dye which may be used is preferably adjusted to a level within the preferred range mentioned above by one skilled in the art such that the hair colour from such mixtures will still deliver reversible colour change properties in accordance with the invention.

In the basic hair dye composition, the direct dye of formula (I) capable of a reversible color change of hair in an aqueous medium exhibits high storage stability within a wide pH range such as from 2 to 11 which is a pH range employed ordinarily for hair dyes, so that the basic hair dye composition can be used freely in the above-described pH range. Use in a pH range of 5 or greater is however preferred from the viewpoint of dyeing properties. Moreover, owing to high stability of the direct dye against an alkali agent, the hair dye composition can be preferably used at a pH above 8, more preferably in a pH range of from 8 to 11 which permits a high dyeing power, and even after storage for a long period of time, it exhibits high dyeing power without decomposition of the direct dye.

Examples of the alkali agent that may be used in the dyeing composition include ammonia, alkanolamines such as monoethanolamine and isopropanolamine or salts thereof, guanidium salts such as guanidine carbonate and hydroxide salts such as sodium hydroxide and sodium carbonate. The alkali agent is preferably added in an amount of from 0.01 to 20 wt. %, more preferably from 0.1 to 10 wt. %, even more preferably from 0.5 to 5 wt. % based on the whole composition.

Since in a basic hair dye composition, a dye such as dye of formula (I) capable of a reversible color change of hair in an aqueous medium has high stability against an oxidizing agent, it can be applied to the hair after mixing with an oxidizing agent. In other words, it may be provided in a form composed of a first component part containing the dye of formula (I) capable of a reversible color change of hair in an aqueous medium and a second component part containing an oxidizing agent. In this case, hair dyeing and bleaching may be carried out simultaneously, which facilitates more vivid hair dyeing.

Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred for hair bleaching properties, stability of the dye and availability. It is also preferred to use a combination of hydrogen peroxide with at least one of the above mentioned other oxidizing agents. The oxidizing agent is preferably added in an amount of from 0.5 to 10 wt. %, more preferably from 1 to 8 wt. %, based on the whole composition. The mixing ratio of the first component part containing the dye (I) capable of a reversible color change of hair in an aqueous medium with the oxidizing-agent-containing second component part preferably ranges from 2:1 to 1:3 in terms of a volume ratio.

Addition of a polyol, polyol alkyl ether, cationic or amphoteric polymer or silicone to the basic hair dye composition is preferred, because the resulting composition can dye the hair uniformly as well as have improved cosmetic effects of the hair.

In addition to the above-described components, those ordinarily employed as a raw material for cosmetics may be added to the basic hair dye composition. Examples of such optional components include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, anionic surfactants, protein derivatives, amino acids, antiseptics, chelating agents, stabilizing agents, antioxidants, plant extracts, crude drug extracts, vitamins, colourants, perfumes and ultraviolet absorbers.

The basic hair dye composition can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The dye (I) capable of a reversible color change of hair in an aqueous medium may be incorporated in either one or both of these component parts of the two-part or three-part composition. When the basic hair dye composition is a one-part type, it is applied to the hair directly, while the two- or three-part type is applied to the hair after mixing these parts upon hair dyeing.

No particular limitation is imposed on the form of the basic hair dye composition. Examples include powder, transparent liquid, emulsion, cream, gel, paste, aerosol, and aerosol foam. It preferably has a viscosity of 2000 to 100000 mPa·s in the stage of application to the hair (after mixing of all the component parts when the composition is a two-part or three-part type). The viscosity is measured at 20° C. by using a Brookfield rotary viscosimeter with a spindle No. 5 at 5 rpm.

After having the hair dyed with the dyeing composition of formula (I) capable of reversible colour change of hair in an aqueous medium as described herein, the colour may be changed to a second colour by application of an aqueous acid formulation, not containing substantially any dye. The acid formulation may be in the form of an acidic shampoo, spray, gel, cream, lotion and the like, wherein the pH value of this acid formulation is preferably within the range of 5 to 1, more preferably 4 to 1.5 and even more preferably 3 to 2. A typical example of an acid formulation contains water and optionally a lower alcohol such as ethanol or isopropanol and additionally an acid that provides the above mentioned pH range. It is preferable to use a weak acid and to make the acid formulation into a buffering system. It is preferred to use organic acids such as lactic acid or citric acid or mineral acids, such as aqueous hydrochloric acid as the acidic substance capable of adjusting the pH to the above range.

No further substance must be present in such an acid formulation. However, it is of course possible to add the usual further ingredients to this acid formulation such as hair conditioners, surfactants, moisturizing agents, perfumes, solvents, and the like.

If these additional ingredients are used, these may be the same as the ingredients illustrated above with respect to the hair dyeing composition that contains at least one dye of formula (I) capable of a reversible color change of hair in an aqueous medium.

After the application of such an acid formulation, the hair is optionally rinsed with water and then optionally dried in a usual manner.

If later on the consumer wants to return the hair to the original post dyed colour, an aqueous alkaline formulation not containing substantially any dye may be applied onto the hair.

Such an alkaline formulation preferably has a pH value of 7 to 11, more preferably 7.5 to 10.5, and even more preferably 8 to 10.5.

Such a formulation contains water and an alkaline substance such as sodium hydroxide, potassium hydroxide, sodium carbonate, ammonium carbonate, or any other alkaline substance that may be used to be applied onto the hair. Additionally, it may also comprise a lower alcohol such as ethanol or isopropanol. Of course, this alkaline formulation may also comprise the commonly used ingredients in addition to the above mentioned essential ingredient, and those additives that are listed above with respect to the acid formulation and the basic hair dye composition respectively, may be used. It is preferable to use a weak alkaline substance and to make the alkaline formulation into a buffering system.

After the application of this alkaline formulation, the hair is optionally rinsed and optionally dried in a conventional manner. After performing this alkaline treatment, the hair returns substantially to the original colour that was obtained after using the above described dyeing composition containing at least one of the dyes of formula (I) capable of a reversible color change of hair in an aqueous medium.

The above procedures may be repeated (e.g. subsequently treating the hair again with an aqueous acid formulation not containing substantially any dye and/or subsequently treating the hair again with an aqueous alkaline formulation not containing substantially any dye) as often as desired by the consumer and the hair colour will be changed accordingly.

The present invention will be described in greater detail by referring to the examples and comparative examples. The following examples further describe and demonstrate embodiments of the present invention. The examples are given solely for purpose of illustration and are not to be construed as limitations of the present invention.

EXAMPLE I

1. Synthesis Example

A synthesis example of a compound represented by formula (I) and capable of a reversible color change of hair is described below.

Synthesis of Listed Compound Dye 1

Dye 1 is synthetically prepared according to the following scheme.

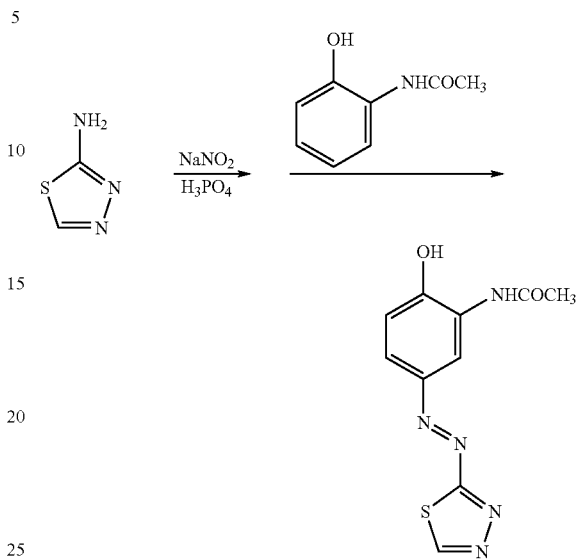

2-Amino-1,3,4-thiadiazole (4.30 g; 42.5 mmol) is added to phosphoric acid (120 ml), and the resulting mixture is agitated under cooling in ice water. Sodium nitrite (2.84 g; 41.1 mmol) in crystal form is added to the mixture, which is agitated for 1.5 hours. 2-Acetylaminophenol (4.70 g; 31.1 mmol) is added to methanol (60 ml), and the resulting mixture is agitated under cooling in ice water, to which is then gradually added the diazo solution prepared above in a dividend manner over 2 hours. After agitation under cooling for one hour and agitation at room temperature for another hour, water (240 ml) is added to the reaction mixture, for agitation for 2 hours. The deposited crystal is filtered, rinsed in water and dried, to recover the listed compound Dye 1 as crystals in an amount of 7.9 g (yield of 96%).

2) Basic Dyeing of the Hair

The dye of formula (I) capable of a reversible color change of hair in an aqueous medium can be dissolved into a mainly aqueous formulation containing alkaline peroxide and can be applied in the form of a composition of formulation A to undamaged white goat hair.

| Formulation A | |
|---|---:|
| Dye formula (I)* | 0.2 g |
| Benzyl Alcohol | 5.0 g |
| Sodium Lauryl Sulphate | 0.01 g |
| Ammonium Hydroxide (25%) | 3.0 g |
| Hydrogen Peroxide (50%) | 6.0 g |
| Water (balance) | up to 100 g |
| pH | 10.0 |

*capable of a reversible color change of hair

The dye mixture can be applied to undamaged white goat hair at 50° C. for 15 min. or 30° C. for 30 min. Approximately 1 g of formulation A is used per gram of hair. After the completion of the dyeing time, the tresses may be rinsed with water, shampoo washed and then dried. The colour of the tresses can then be recorded. L, a and b values of the tresses before and after the colouring treatment can be measured by a Minolta colour-measuring instrument and the value of delta E, which is a known measure for the chroma, can be calculated according to the following equation:

$$\Delta E = (\Delta L^2 + \Delta a^2 + \Delta b^2)^{1/2}$$

3) Measurement of pKa Value

The pKa values of the dyes can be determined by the following method. The dye is dissolved in a solution of a DMF/water (1/1) volume ratio to a final concentration of $2 \times 10^{-5}$ mol/l. After adjusting the resulting solution to pH 2, using 1.0 mol/l hydrochloric acid, the solution is titrated with aqueous 1.0 mol/l sodium hydroxide solution. Recording the change of the visible ultra-violet absorption spectrum, the inflection point can be determined by regression analysis.

The following examples describe the method of effecting a reversible change of the colour of the hair dyed with the dye composition of the present invention.

EXAMPLE II

The following experiments were performed by using the dyes of formula I. The data shows the relationship between pKa of the dyes and their ability to undergo colour change as described in the application. All of the dyes have the formula I, but only dyes within a certain pKa range are capable of reversible colour change of hair in which the hair changes to a second colour by treatment with the acidic formulation defined in Table 2. The dyeing solutions each had the following compositions:

TABLE 1

| Ingredient | % Weight |
| --- | --- |
| Dye of formula (I) | 0.2% |
| Ammonium Hydroxide (28%) | 3% |
| Benzyl Alcohol | 5% |
| Sodium Lauryl Sulphate | 0.01% |
| Hydrogen Peroxide (50%) | 6% |
| Water | up to 100% |

Adjusted to pH 10 with lactic acid.

The dye solution is applied in a 1:1 weight ratio to untreated white goat hair at 30° C. for 20 min. After this time, the tresses are shampoo rinsed, dried and the colour measured.

The tresses were then run through the following protocol:
 a. Acidic Gel (see Table 2a below) was applied in a ratio of 1 g per 1 g of hair tress for 1 min.
 b. The hair tress was rinsed with water and dried, and the colour and delta E vs. the original dyed colour was then measured.
 c. An alkaline cream (see Table 2b below) was applied in a ratio of 1 g per 1 g of the hair tress for 1 min.
 d. The hair tress was rinsed and dried, and the colour and delta E vs. the original dyed colour was then measured.

TABLE 2a

Acidic Gel used in Example II

| Ingredient | Weight % |
| --- | --- |
| Propylene Carbonate | 25% |
| EtOH | 5% |
| Lactic Acid | 5% |
| NaOH (32%) | 0.3% |
| Xanthum Gum | 1% |

TABLE 2a-continued

Acidic Gel used in Example II

| Ingredient | Weight % |
| --- | --- |
| Water | up to 100% |
| pH | adjusted to 3. |

TABLE 2b

Alkaline Cream used in Example II

| Ingredient | % Weight |
| --- | --- |
| Cetearyl Alcohol | 5.4 |
| Sodium Cetearyl Sulfate | 0.6 |
| Stearamide MEA | 1.1 |
| Cocamide MEA | 1.1 |
| Oleth-5 | 2.5 |
| Oleic Acid | 1.3 |
| Propylene Glycol | 0.5 |
| Sodium Lauryl Sulfate | 0.3 |
| Ammonium Hydroxide | 2.4 |
| $H_2O_2$ | 3 |
| Water | To 100 |

The delta E ($\Delta E$) colour changes vs. the original dyed color were measured, and the results thereof are shown in Tables 3a and 3b below.

TABLE 3a

Red and Yellow Dyes

| Dye | pKa | Treatment | L | a | b | Delta E Colour Change |
| --- | --- | --- | --- | --- | --- | --- |
| 34* | 2.9 | Dyed | 75 | 19 | 69 | |
| | 2.9 | Acid Solution | 74 | 18 | 68 | 2 |
| | 2.9 | Alkali Solution | 75 | 18 | 69 | 1 |
| 25* | 3.0 | Dyed | 40 | 51 | −17 | |
| | 3.0 | Acid Solution | 41 | 52 | −16 | 1 |
| | 3.0 | Alkali Solution | 41 | 51 | −17 | 1 |
| 29* | 3.3 | Dyed | 26 | 50 | −2 | |
| | 3.3 | Acid Solution | 26 | 52 | −3 | 2 |
| | 3.3 | Alkali Solution | 26 | 51 | −3 | 1 |
| 26* | 3.5 | Dyed | 27 | 50 | 11 | |
| | 3.5 | Acid Solution | 27 | 51 | 12 | 1 |
| | 3.5 | Alkali Solution | 28 | 50 | 11 | 1 |
| 30* | 3.8 | Dyed | 33 | 57 | 21 | |
| | 3.8 | Acid Solution | 32 | 55 | 22 | 2 |
| | 3.8 | Alkali Solution | 34 | 56 | 21 | 1 |
| 34* | 4.2 | Dyed | 79 | −1 | 56 | |
| | 4.2 | Acid Solution | 80 | −2 | 54 | 2 |
| | 4.2 | Alkali Solution | 78 | −2 | 56 | 1 |
| 35* | 4.7 | Dyed | 77 | 13 | 75 | |
| | 4.7 | Acid Solution | 78 | 11 | 73 | 3 |
| | 4.7 | Alkali Solution | 76 | 12 | 74 | 2 |
| 28* | 4.8 | Dyed | 28 | 43 | 13 | |
| | 4.8 | Acid Solution | 27 | 43 | 13 | 1 |
| | 4.8 | Alkali Solution | 29 | 43 | 13 | 1 |
| 31* | 5.0 | Dyed | 36 | 54 | 22 | |
| | 5.0 | Acid Solution | 36 | 53 | 24 | 2 |
| | 5.0 | Alkali Solution | 37 | 53 | 23 | 1 |
| 36* | 5.2 | Dyed | 85 | −5 | 57 | |
| | 5.2 | Acid Solution | 85 | −6 | 57 | 1 |
| | 5.2 | Alkali Solution | 84 | −4 | 56 | 2 |
| 32* | 5.2 | Dyed | 36 | 62 | −2 | |
| | 5.2 | Acid Solution | 36 | 62 | −1 | 1 |
| | 5.2 | Alkali Solution | 37 | 62 | −2 | 1 |
| 22 | 5.5 | Dyed | 77 | 12 | 85 | |
| | 5.5 | Acid Solution | 79 | 2 | 89 | 11 |
| | 5.5 | Alkali Solution | 77 | 10 | 85 | 2 |

TABLE 3a-continued

Red and Yellow Dyes

| Dye | pKa | Treatment | L | a | b | Delta E Colour Change |
|---|---|---|---|---|---|---|
| 2 | 5.5 | Dyed | 36 | 50 | −6 | |
| | 5.5 | Acid Solution | 50 | 35 | 10 | 26 |
| | 5.5 | Alkali Solution | 38 | 49 | −7 | 2 |
| 23 | 5.8 | Dyed | 80 | −10 | 53 | |
| | 5.8 | Acid Solution | 81 | −8 | 41 | 12 |
| | 5.8 | Alkali Solution | 81 | −10 | 53 | 1 |
| 24 | 5.9 | Dyed | 77 | 9 | 68 | |
| | 5.9 | Acid Solution | 81 | −2 | 64 | 12 |
| | 5.9 | Alkali Solution | 78 | 8 | 67 | 2 |
| 7 | 5.9 | Dyed | 36 | 55 | 14 | |
| | 5.9 | Acid Solution | 43 | 57 | 25 | 14 |
| | 5.9 | Alkali Solution | 38 | 55 | 15 | 2 |
| 1 | 6.0 | Dyed | 46 | 60 | 20 | |
| | 6.0 | Acid Solution | 51 | 56 | 32 | 14 |
| | 6.0 | Alkali Solution | 47 | 60 | 21 | 1 |
| 5 | 6.1 | Dyed | 36 | 52 | 0 | |
| | 6.1 | Acid Solution | 46 | 45 | 20 | 23 |
| | 6.1 | Alkali Solution | 37 | 52 | −1 | 1 |
| 6 | 6.2 | Dyed | 44 | 32 | −2 | |
| | 6.2 | Acid Solution | 53 | 21 | 20 | 24 |
| | 6.2 | Alkali Solution | 44 | 32 | −3 | 1 |
| 21 | 6.4 | Dyed | 84 | −5 | 57 | |
| | 6.4 | Acid Solution | 79 | 3 | 61 | 10 |
| | 6.4 | Alkali Solution | 84 | −4 | 58 | 1 |

*Comparative Examples of dyes of formula (I) not capable of reversible color change of hair

TABLE 3b

Blue Dyes

| Dye | pKa | Treatment | L | a | b | Delta E Colour Change |
|---|---|---|---|---|---|---|
| 27* | 3.0 | Dyed | 32 | 10 | −31 | |
| | 3.0 | Acid Solution | 32 | 8 | −29 | 3 |
| | 3.0 | Alkaline Solution | 34 | 10 | −31 | 2 |
| 39* | 3.9 | Dyed | 55 | −5 | −17 | |
| | 3.9 | Acid Solution | 56 | −5 | −16 | 3 |
| | 3.9 | Alkaline Solution | 58 | −5 | −15 | 4 |
| 12 | 4.0 | Dyed | 39 | 7 | −29 | |
| | 4.0 | Acid Solution | 44 | −2 | −1 | 30 |
| | 4.0 | Alkaline Solution | 41 | 7 | −27 | 3 |
| 8 | 4.4 | Dyed | 44 | 12 | −37 | |
| | 4.4 | Acid Solution | 52 | 27 | −1 | 14 |
| | 4.4 | Alkaline Solution | 45 | 12 | −35 | 3 |
| 13 | 4.7 | Dyed | 31 | 20 | −28 | |
| | 4.7 | Acid Solution | 32 | 11 | −14 | 17 |
| | 4.7 | Alkaline Solution | 33 | 20 | −27 | 2 |
| 10 | 5.0 | Dyed | 52 | −31 | −5 | |
| | 5.0 | Acid Solution | 49 | −18 | −12 | 15 |
| | 5.0 | Alkaline Solution | 54 | −31 | −5 | 2 |
| 9 | 6.1 | Dyed | 23 | 12 | −32 | |
| | 6.1 | Acid Solution | 30 | 27 | −1 | 35 |
| | 6.1 | Alkaline Solution | 25 | 12 | −30 | 3 |
| 3 | 6.5 | Dyed | 19 | 16 | −17 | |
| | 6.5 | Acid Solution | 29 | 11 | 15 | 34 |
| | 6.5 | Alkaline Solution | 20 | 12 | −17 | 1 |
| 4 | 7.0 | Dyed | 57 | −9 | −10 | |
| | 7.0 | Acid Solution | 68 | −1 | 23 | 36 |
| | 7.0 | Alkaline Solution | 59 | −9 | −9 | 2 |

*Comparative example of dyes of formula (I) not capable of reversible colour change of hair The results shown in Table 3a and 3b clearly show that only dyestuffs of formula (I) and of a certain pKa can undergo a colour change of the hair on application of the simple acidic formulation in Table 2. The invention is limited to these dyestuffs, although the dyestuffs of the invention can be used in combination with dyestuffs not of the invention, such as those in Table 3a and 3b not undergoing colour change. The pKa range is different for blue dyestuffs compared to red and yellow dyes.

EXAMPLE III

The dyes of formula (I) capable of a reversible color change can be dissolved into the following alkaline colouring cream formulations (I) through (IV). Formulation (I) contains only dyes of formula (I) capable of reversible color change of hair. Formulations (II)–(IV) contain at least one dye of formula (I) capable of a reversible color change of hair and at least one dye of formula (I) not capable of a reversible color change of hair. Formulations (I)–(IV) are examples of the invention. Formulations (V) and (VI) are comparative examples made up only of dyestuffs which are not part of the invention (see Table 4):

TABLE 4

| Ingredient | I | II | III | IV | V** | VI** |
|---|---|---|---|---|---|---|
| Dye 9 | 0.2 | 0.2 | / | / | / | / |
| Dye 23 | 0.1 | / | / | / | / | / |
| Dye 5 | 0.1 | / | / | / | / | / |
| Dye 40* | / | 0.1 | 0.1 | 0.2 | / | / |
| Dye 30* | / | 0.02 | 0.02 | 0.05 | / | / |
| Dye 15 | / | / | 0.2 | 0.2 | / | / |
| Cationic dye 2* | / | / | / | / | 0.05 | / |
| Cationic dye 1* | / | / | / | / | 0.1 | / |
| Oxidative dye 1 (p-TD)* | / | / | / | / | / | 0.2 |
| Oxidative dye 2 (m-AP)* | / | / | / | / | / | 0.1 |
| Oxidative dye 3 Resorcinol* | / | / | / | / | / | 0.1 |
| Cetearyl Alcohol | 5.4 | 5.4 | 5.4 | 5.4 | 5.4 | 5.4 |
| Sodium Cetearyl Sulfate | 0.6 | 0.6 | 0.6 | 0.6 | 0.6 | 0.6 |
| Stearamide MEA | 1.1 | 1.1 | 1.1 | 1.1 | 1.1 | 1.1 |
| Cocamide MEA | 1.1 | 1.1 | 1.1 | 1.1 | 1.1 | 1.1 |
| Oleth-5 | 2.5 | 2.5 | 2.5 | 2.5 | 2.5 | 2.5 |
| Oleic Acid | 1.3 | 1.3 | 1.3 | 1.3 | 1.3 | 1.3 |
| Propylene Glycol | 0.5 | 0.5 | 0.5 | 0.5 | 0.5 | 0.5 |
| Sodium Lauryl Sulfate | 0.3 | 0.3 | 0.3 | 0.3 | 0.3 | 0.3 |
| Ammonium Hydroxide | 2.4 | 2.4 | 2.4 | 2.4 | 2.4 | 2.4 |
| $H_2O_2$ | 3 | 3 | 3 | 3 | 3 | 3 |
| Water | To 100 | To 100 | To 100 | To 100 | To 100 | To 100 |

*Dyes that do not have the capability of reversible colour change of hair in an aqueous medium.
**Comparative Examples The above compositions were applied in a 1 to 1 ratio to undamaged goat tresses at 30 degrees Celsius for 30 minutes. The tresses were then rinsed with water (pH 7), shampoo washed and then dried. The colour of the tresses was then recorded. L, a and b values of the tresses before and after the colouring can be measured in the same way as the earlier Examples.

Next, the acidic gel formulation (Table 5) was applied (ratio of 1 g per 1 g of hair) for 1 minute. The Tress was rinsed with water and dried, and the colour and delta E color change vs. the original dyed color was then measured. The tress was rinsed with water and the alkaline cream (see Table 6) was applied (ratio of 1 g per 1 g of hair) for 1 minute. The tress was rinsed and dried, and the colour and delta E vs. the original dyed color was then measured.

The colours achieved with the basic dyeing compositions and the reversible changes thereof by using the acidic gel and alkaline cream formulations are shown in Table 7 below.

TABLE 5

Example acidic gel composition:

| Ingredient | % |
|---|---|
| Ethanol | 5 |
| Lactic Acid | 2.5 |
| Xanthum Gum | 1.5 |
| Dimethicone Copolyol | 1 |
| Water | Up to 100 |
| Sodium Hydroxide | Adjust until pH 2.5 |

TABLE 6

Example alkaline cream composition:

| Ingredient | % |
|---|---|
| Cetearyl Alcohol | 7.0 |
| Octyldodecanol | 1.0 |
| Oleyl Alcohol | 2.0 |
| Sodium Lauryl Sulfate | 2.0 |
| Ammonia (25%) | 6.25 |
| Ammonium Bicarbonate | 0.41 |
| Water | To 100 |

TABLE 7

| Formulation | Treatment | L | a | b | ΔE | Colour |
|---|---|---|---|---|---|---|
| / | Untreated | 84 | 0 | 12 | / | White |
| I | Dyed | 36 | 36 | −1 | / | Violet-Red |
| I | Acid Gel | 45 | 37 | 12 | 16 | Copper |
| I | Alkali Cream | 37 | 37 | 0 | 1.5 | Violet-Red |
| II | Dyed | 50 | 6 | 8 | / | Ash Green |
| II | Acid Gel | 56 | 20 | 22 | 21 | Light Copper |
| II | Alkali Cream | 52 | 5 | 8 | 2 | Ash Green |
| III | Dyed | 32 | 9 | −11 | / | Dark Ash |
| III | Acid Gel | 37 | 7 | 7 | 19 | Light Brown |
| III | Alkali Cream | 32 | 7 | −10 | 2 | Dark-Ash |
| IV | Dyed | 30 | 10 | −2 | / | Dark auburn |
| IV | Acid Gel | 35 | 14 | 10 | 14 | Ash Brown |
| IV | Alkali Cream | 31 | 11 | 0 | 2.5 | Dark Auburn |
| V* | Dyed | 38 | 57 | 24 | / | Bright Red |
| V* | Acid Gel | 40 | 59 | 26 | 4 | Bright Red |
| V* | Alkali Cream | 39 | 60 | 27 | 5 | Bright Red |
| VI* | Dyed | 31 | 4 | 10 | / | Brown |
| VI* | Acid Gel | 31 | 3 | 10 | 1 | Brown |
| VI* | Alkali Cream | 33 | 4 | 10 | 2 | Brown |

*Comparative Examples - Not part of the invention

As can be seen in Table 7, only examples containing at least one dye of formula (I) capable of a reversible color change of hair undergo the reversible color change. Formulations (I)–(IV) all underwent color changes of delta E>10 on application of the acidic gel in Table 5 and then returned to within delta E>4 of the original color on application of the alkaline cream in Table 6. In contrast, Formulations (V) and (VI), which contained no dyes of formula (I) capable of a reversible color change of hair, underwemt no color change on application of the acid and alkali formulations in Table 5 and Table 6.

EXAMPLE IV

The following gel formulations VII and VIII shown in Table 8 were applied to undamaged white goat hair at 30° C. for 30 min.

TABLE 8

| | Formulation | |
|---|---|---|
| | VII | VIII |
| Dye 9* | 0.10 g | 0.1 g |
| Dye 33** | / | 0.20 g |
| Dye 30** | 0.20 g | 0.03 g |
| Ammonium hydroxide −25% | 6 g | 6 g |
| Na$_2$CO$_3$ | 1 g | 1 g |
| Benzyl Alcohol | 2 g | 2 g |
| Isopropanol | 4 g | 4 g |
| Hydrogen Peroxide (50%) | 6 g | 6 g |
| Xanthum Gum | 1 g | 1 g |
| Water up to | 100 g | 100 g |
| pH*** | 10 | 10 |

*Dye of formula (I) capable of a reversible color change of hair
**Dye of formula (I) not capable of a reversible color change of hair
***pH adjusted with sodium hydroxide and/or lactic acid.

The hair was then dried and measured. The hair tresses were then run through the following protocol:

a. Formulation A (see Table 9 below) was applied as a spray (ratio of 1 g of hair) for 1 min.

b. The hair tress was rinsed with water and dried, and the colour and delta E vs. the original dyed colour was then measured c. Formulation B (see table 9 below) was applied as a spray (ratio of 1 g per 1 g of hair) for 1 min.

d. The hair tress was rinsed with water and dried, and the colour and delta E vs. the original dyed colour was then measured

TABLE 9

| | Formulation | |
|---|---|---|
| | A | B |
| NaOH (1.0 M) | / | 3 g |
| Lactic Acid | 1 g | 1 g |
| Ethanol | 5 g | 5 g |
| Water up to | 100 g | 100 g |
| pH | 3 | 9 |

This protocol was repeated 3 times for tresses dyed with Formulation VII and VIII. The colours achieved with the basic dyeing compositions and the reversible changes thereof by using spray Formulations A or B are shown in Table 10 below.

TABLE 10

| Dye Formulation | Protocol | L | a | b | Delta E (colour change) | Colour |
|---|---|---|---|---|---|---|
| None | Initial Uncoloured Tress | 82 | 0 | 12 | | White |
| VII | Dyed | 20 | 22 | −9 | | Violet |
| VII | Treatment A applied | 28 | 35 | 1 | 15 | Red |
| VII | Treatment B applied | 21 | 22 | −9 | 1 | Violet |
| VII | Treatment A applied | 29 | 35 | 1 | 16 | Red |
| VII | Treatment B applied | 21 | 22 | −9 | 1 | Violet |
| VII | Treatment A applied | 29 | 35 | 1 | 16 | Red |
| VII | Treatment B applied | 22 | 22 | −9 | 2 | Violet |

TABLE 10-continued

| Dye Formulation | Protocol | L | a | b | Delta E (colour change) | Colour |
|---|---|---|---|---|---|---|
| VIII | Dyed | 29 | 7 | 3 | | Ash Brown |
| VIII | Treatment A applied | 36 | 19 | 16 | 19 | Copper Brown |
| VIII | Treatment B applied | 30 | 7 | 3 | 1 | Ash Brown |
| VIII | Treatment A applied | 37 | 19 | 16 | 20 | Copper Brown |
| VIII | Treatment B applied | 31 | 7 | 3 | 1 | Ash Brown |
| VIII | Treatment A applied | 37 | 19 | 16 | 20 | Copper Brown |
| VIII | Treatment B applied | 32 | 7 | 3 | 2 | Ash Brown |

Table 10 shows that Formulations according to the invention can undergo color changes of greater than delta E of 10 on application of an acidic spray and can return to within a delta E less of than 4 of the original dyed color on application of an alkaline spray. This reversible color change can be repeated multiple times by further applications of acid and alkaline treatments.

EXAMPLE V

As additional preferred embodiments of the present invention, the following compositions may be used as aqueous acid formulations:

1) Acid Styling Mist

| | Wt. % |
|---|---|
| Maleic Acid | 2.5 |
| Lactic Acid | 2.5 |
| Stearyltrimethylammonium chloride | 0.25 |
| 2-Benzyloxyethanol | 2.5 |
| Ethanol | 4.5 |
| Water | Balance |

The pH is adjusted to 3.7 by adding small amounts of aqueous sodium hydroxide.

2) Acid Hair Conditioner

| | Wt. % |
|---|---|
| Lactic acid | 4 |
| Polypropylene glycol (molecular weight: 400) | 1 |
| Behenyltrimethylammonium chloride | 1.7 |
| Behenyl alcohol | 5.1 |
| Methyl polysiloxane (SH500-5000CS) | 3 |
| Isopropyl palmitate | 1 |
| Dipentaerythritol fatty acid ester | 0.1 |
| Benzyloxyethanol | 0.3 |
| Hydroxyethyl cellulose | 0.2 |
| 48% NaOH | 0.2 |
| Purified water | Balance |
| pH (when diluted 20-fold by weight) | 2.7 |

3) Acid Shampoo

| | Wt. % |
|---|---|
| Sodium lauryl ethoxy (2) sulfate | 10 |
| Sodium lauryl sulfate | 5 |
| Cationic guar gum | 0.3 |
| Malic acid | 0.75 |
| Lactic acid | 0.1 |
| Sodium chloride | 0.5 |
| Benzyl alcohol | 0.1 |
| Cationic cellulose | 0.3 |
| Purified water | Bal. |
| pH (when diluted 20-fold by weight) | 3.4 |

What is claimed is:

1. A method of effecting a change of colour of hair, comprising the following steps:
   (a) dyeing the hair to a first colour with an aqueous alkaline dyeing composition comprising at least one azo dye of formula (I):

$$A-N=N-B \qquad (I)$$

wherein A is a monovalent group, which binds an azo group with a carbon atom, and which is free of carboxy (—CO$_2$H) groups, sulfo groups (SO$_3$H), or quaternary ammonium groups, and B is a monovalent group containing a dissociative proton and, which is free of carboxy (—CO$_2$H) groups, sulfo groups (—SO$_3$H), or quaternary ammonium groups, wherein the azo dye is capable of reversible colour change of hair in an aqueous medium;
   (b) rinsing the dyed hair with water and
   (c) subsequently treating the dyed hair with an aqueous acid formulation not containing substantially any dye, wherein the colour of the hair is changed to a second colour.

2. The method according to claim 1, further comprising a step (d) of treating the hair with an aqueous alkaline formulation not containing substantially any dye, whereby the hair colour changes to substantially the first colour resulting from the dyeing step (a).

3. The method according to claim 1, wherein the A group of formula (I) contains a proton with a pKa value from 4 to 8 for blue dyes.

4. The method according to claim 3, wherein the pKa value is from 4.2 to 7.8.

5. The method according to claim 3, wherein the pKa value is from 4.4 to 7.5.

6. The method according to claim 1, wherein the A group of formula (I) contains a proton with a pKa value from 5.3 to 8 for red and/or yellow dyes.

7. The method according to claim 5, wherein the pKa value is from 5.4 to 7.5.

8. The method according to claim 5, wherein the pKa value is from 5.5 to 7.0.

9. The method according to claim 1, wherein the aqueous alkaline dyeing composition further comprises hydrogen peroxide.

10. The method according to claim 1, wherein the colour change of the hair, expressed as a delta E value, after acid treatment of the hair is greater than 10.

11. The method according to claim 1, wherein the azo dye of formula (I) is at least one selected from the group consisting of the following dyes, and mixtures thereof:

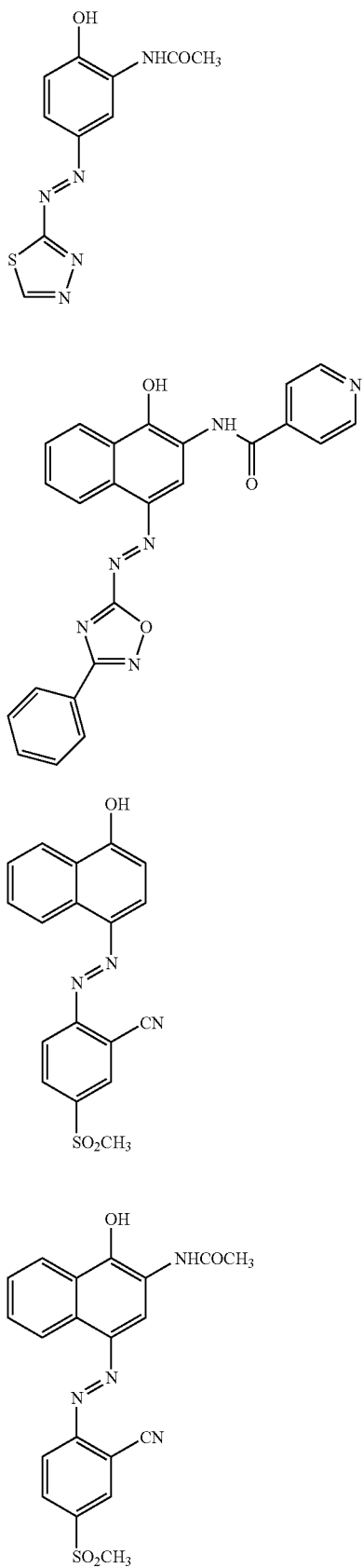
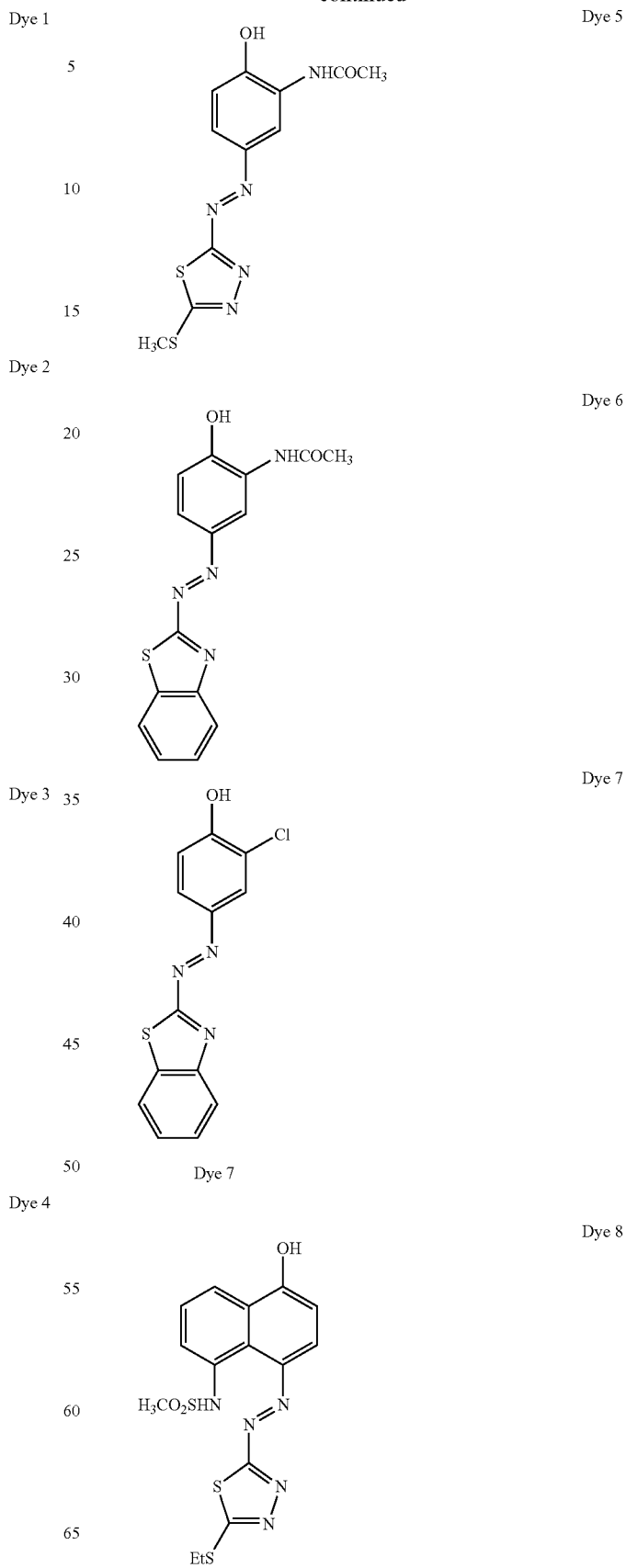

Dye 9
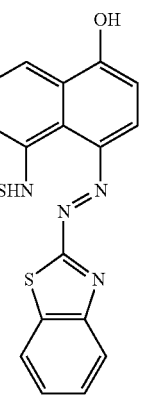
Dye 13
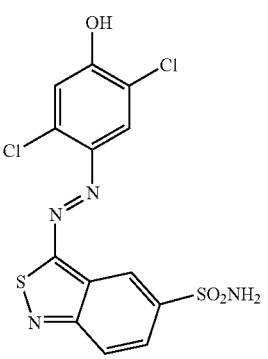
Dye 10
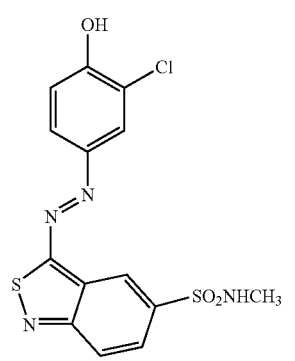
Dye 14
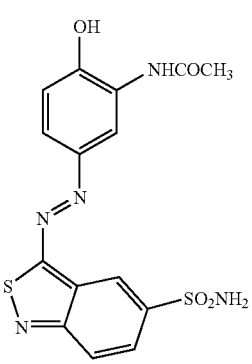
Dye 11
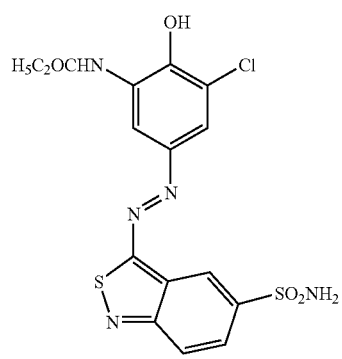
Dye 15
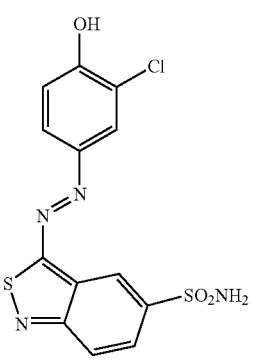
Dye 12
Dye 16
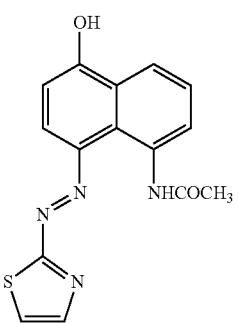

-continued
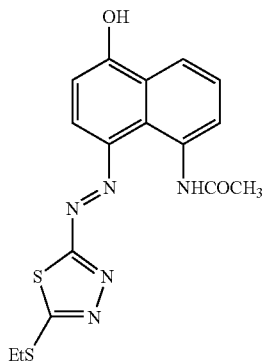
Dye 17
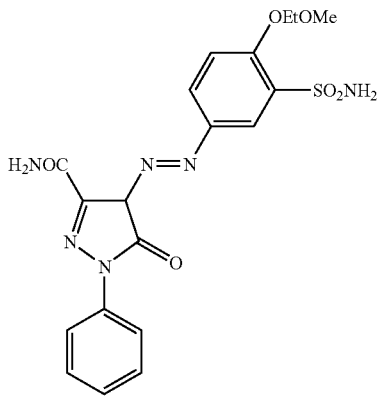
Dye 21
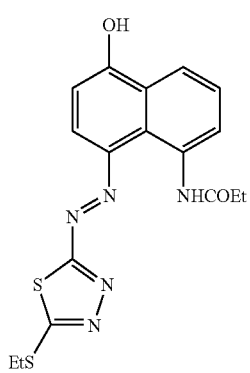
Dye 18
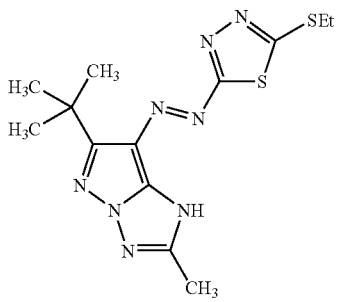
Dye 22
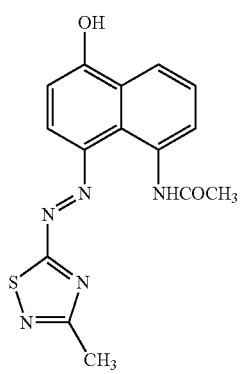
Dye 19
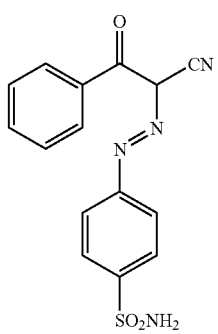
Dye 23
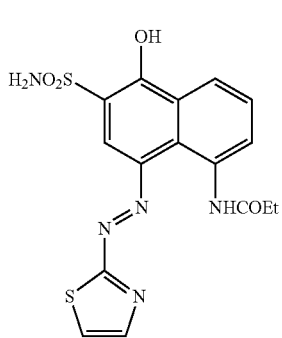
Dye 20
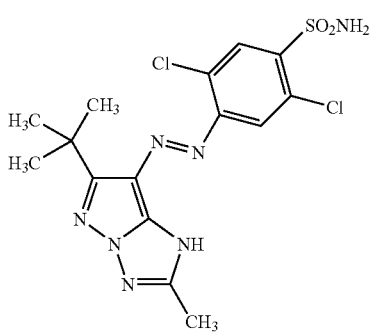
Dye 24

12. The method according to claim 1 wherein the aqueous acid formulation used in step (c) contains an acidic substance to adjust the pH of the formulation to between pH 5 and pH 1.

13. The method according to claim 2, wherein the alkaline formulation used in step (d) contains an alkaline substance to adjust the pH of the formulation to 7 to 11.

14. The method according to claim 1, wherein the aqueous alkaline dyeing composition of step (a) further comprises additional dyes which are not capable of reversible colour change of hair in an aqueous medium.

15. The method according to claim 2, further comprising the step of:
(e) treating the hair with an aqueous acid formulation not containing substantially any dye, whereby the hair colour changes to substantially the second colour resulting from the dyeing step (c).

* * * * *

UNITED STATES PATENT AND TRADEMARK OFFICE
CERTIFICATE OF CORRECTION

PATENT NO. : 7,198,651 B2
APPLICATION NO. : 10/996376
DATED : April 3, 2007
INVENTOR(S) : Dominic Pratt et al.

It is certified that error appears in the above-identified patent and that said Letters Patent is hereby corrected as shown below:

On The Title Page, item 30, Foreign Application Priority Data, "03027429" should read --03027429.4--

Signed and Sealed this

Twelfth Day of June, 2007

JON W. DUDAS
*Director of the United States Patent and Trademark Office*